US008575392B2

(12) United States Patent
Yoshimoto et al.

(10) Patent No.: US 8,575,392 B2
(45) Date of Patent: Nov. 5, 2013

(54) CHARGE-TRANSPORTING VARNISH

(75) Inventors: Takuji Yoshimoto, Funabashi (JP); Tomohisa Yamada, Funabashi (JP); Taku Kato, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 640 days.

(21) Appl. No.: 12/373,426

(22) PCT Filed: Jul. 17, 2007

(86) PCT No.: PCT/JP2007/064060
§ 371 (c)(1),
(2), (4) Date: Jan. 12, 2009

(87) PCT Pub. No.: WO2008/010474
PCT Pub. Date: Jan. 24, 2008

(65) Prior Publication Data
US 2009/0269688 A1   Oct. 29, 2009

(30) Foreign Application Priority Data

Jul. 18, 2006 (JP) ................................. 2006-195226

(51) Int. Cl.
*C07C 211/00* (2006.01)
(52) U.S. Cl.
USPC ............ 564/305; 564/248; 252/500; 549/362
(58) Field of Classification Search
None
See application file for complete search history.

(56) References Cited

U.S. PATENT DOCUMENTS

| 5,273,841 | A | 12/1993 | Yamamoto et al. | |
| 7,771,842 | B2 * | 8/2010 | Yoshimoto et al. | 428/690 |
| 7,862,747 | B2 * | 1/2011 | Yoshimoto et al. | 252/500 |
| 2005/0079533 | A1 | 4/2005 | Samuelson et al. | |
| 2005/0147991 | A1 | 7/2005 | Samuelson et al. | |
| 2006/0225611 | A1 * | 10/2006 | Kato et al. | 106/236 |

FOREIGN PATENT DOCUMENTS

| DE | 2262743 A1 * | 7/1973 |
| DE | 42 21 189 A1 | 1/1993 |
| EP | 1 638 372 A1 | 3/2006 |
| EP | 1 640 372 A1 | 3/2006 |
| JP | 3-273087 A | 12/1991 |
| JP | 6-52904 A | 2/1994 |
| JP | 6-256509 A | 9/1994 |
| JP | 2005-108828 A | 4/2005 |
| WO | WO-2004/043117 A1 | 5/2004 |
| WO | WO-2004/105446 A1 | 12/2004 |
| WO | WO-2005/000832 A1 | 1/2005 |
| WO | WO-2005/043962 A1 | 5/2005 |
| WO | WO-2005/107335 A1 | 11/2005 |
| WO | WO 2006/006459 A | 1/2006 |
| WO | WO-2006/025342 A1 | 3/2006 |
| WO | WO 2007/049631 A1 | 5/2007 |
| WO | WO 2008/005413 A2 | 1/2008 |

OTHER PUBLICATIONS

Sun et al (Synthetic Metals, 2001, 119(1-3), 313-314).*
European Search Report dated Aug. 18, 2010 for Application No. 07790822.6.
Japanese Office Action mailed Aug. 8, 2012 in corresponding Japanese Application No. 2008-525855.
Rotschova et al., Journal of Chromatography, "Antioxidants and Stabilizers", vol. 216, pp. 251-259 (1981).
S. A. Van Slyke et al., Appl. Phys. Lett. vol. 69 No. 15, Oct. 7, 1996, pp. 2160-2162.
G. Gustafsson et al., Nature, vol. 357, Jun. 11, 1992, pp. 477-479.
Jayesh Bharathan et al., Applied Physics Letters, vol. 72, No. 21, May 25, 1998, pp. 2660-2662.
Junbo Gao et al., Macromol. Rapid Commun., 20, 1999, pp. 560-563.
Miyoko Ochi et al., Bull. Chem. Soc. Jpn., vol. 67, No. 8, Jun. 1994, pp. 1749-1752.

* cited by examiner

*Primary Examiner* — Sudhakar Katakam
(74) *Attorney, Agent, or Firm* — Birch, Stewart, Kolasch & Birch, LLP

(57) ABSTRACT

A charge-transporting varnish comprising a phenylamino-N, N'-diphenylquinonediimine derivative represented by the formula (1) as a charge-transporting substance. It becomes possible to provide a charge-transporting varnish comprising an oxidized oligoaniline, which has a high solubility in various organic solvents and also has a good filtration property because the varnish has no aggregation property.

(1)

(wherein $R^1$ represents a hydrogen atom or a substituted or unsubstituted monovalent hydrocarbon group; and $R^2$ to $R^{19}$ independently represent a hydrogen atom, a hydroxyl group, an amino group, a silanol group, a thiol group, a carboxyl group, a phosphoric acid group, a phosphate ester group, an ester group, a thioester group, an amide group, a nitro group, a substituted or unsubstituted monovalent hydrocarbon group, an organooxy group, an organoamino group, an organosilyl group, an organothio group, an acyl group, a sulfone group or a halogen atom.)

9 Claims, 2 Drawing Sheets

CHARGE-TRANSPORTING VARNISH

TECHNICAL FIELD

This invention relates to a charge-transporting varnish and more particularly, to a charge-transporting varnish including a phenylamino-N,N'-diphenylquinonediimine derivative.

BACKGROUND ART

It has been reported that when a copper phthalocyanine layer (CuPC) layer is provided as a hole injection layer in low molecular weight organic EL (hereinafter abbreviated as OLED) devices, there can be realized improvements in initial characteristics such as a lowering of drive voltage and a luminous efficiency and also in life characteristics (Non-patent Document 1: Applied Physics Letters, United States of America, 1996, Vol. 69, pp. 2160-2162).

On the other hand, with respect to organic EL devices using polymer light-emitting materials (hereinafter referred to as PLED), it has been reported that similar effects as the OLED device can be obtained when using, as a hole transport layer, a thin film of a polyaniline material (Patent Document 1: JP-A 3-273087, and Non-patent Document 2: Nature, United Kingdom, 1992, Vol. 357, pp. 477-479) or a polythiophene material (Non-patent Literature 3: Applied Physics Letters, United States of America, 1998, Vol. 72, pp. 2660-2662).

In recent years, there has been found a charge-transporting varnish which makes use of a highly-soluble low molecular weight oligoaniline material or oligothiophene material and is made of a homogeneous solution completely dissolving the material in an organic solvent. A report has been made that when a hole injection layer obtained from the varnish is inserted into an organic EL device, a flattening effect of an underlying substrate and excellent EL device characteristics are obtained (Patent Document 2: JP-A 2002-151272 and Patent Document 3: WO 2005/043962 Pamphlet).

Such a low molecular weight oligomer compound is in its own low in viscosity, for which if an ordinary organic solvent is used, a process margin in film-forming operations becomes narrow. Accordingly, when using various coating systems such as spin coating, inkjet coating, spray coating and the like and a variety of baking conditions, a difficulty is involved in film formation ensuring high uniformity. Nevertheless, when using different types of additive solvents, adjustment of viscosity and controls of boiling point and vapor pressure become possible, thus enabling film-formed surfaces to have high uniformity correspondingly to various types of coating systems (Patent Document 4: WO 2004/043117 Pamphlet and Patent Document 5: WO 2005/107335 Pamphlet).

The reason why no precipitation of solid matters occurs after addition of various types of solvents as set out above thereby ensuring solution uniformity is based on the high solubility and non-aggregation property of such a low molecular weight oligomer compound. In this sense, the dissolution characteristic of a charge-transporting material to be coated is very important. On the other hand, it has been reported that an oligoaniline compound is oxidized beforehand (preliminary oxidation) for use partly as a quinoid structure, enabling the shortage of a baking time (Patent Document 6: WO 2004/105446 Pamphlet). This technique is highly effective in film formation on a film substrate that would need low temperature baking at 160° C. or below.

However, this preliminarily oxidized oligoaniline compound is low in solubility and high in aggregation property, so that the varnish obtained by use of the compound has, in some case, presented problems on filterability, and uniformity. Polyaniline and oligoaniline compounds generally exhibit the highest solubility in a reduced state (leuco-emeraldin) and the highest conductivity in a semi-oxidized state (emeraldin). On the other hand, when oxidation proceeds excessively, a perniglaniline state results wherein quinoid structures are arranged in sequence, with the result that the conductivity lowers and solubility further lowers.

The preliminarily oxidized polyaniline and oligoaniline compounds are, in most cases, in a mixed state of perniglaniline and emeraldin. Owing to the partly existing perglaniline state, solubility may often lower, aggregation may occur in a solution, and defectives or irregularities may occur upon formation as a film. Accordingly, where preliminarily oxidized polyaniline and oligoaniline compounds are used for the purposes of shortening a baking time, lowering a baking temperature and the like, it is necessary to create an oxidized state wherein a highly dispersed semi-oxidized state is formed without formation of a sequence of quinoid structures. This formation is usually difficult and thus, there has been a demand for solving the problem.

Non-patent Document 1: Applied Physics Letters, United States of America, 1996, Vol. 69, pp. 2160-2162
Non-patent Document 2: Nature, United Kingdom, 1992, Vol. 357, pp. 477-479
Non-patent Document 3: Applied Physics Letters, United States of America, 1998, Vol. 72, pp. 2660-2662
Patent Document 1: JP-A 3-273087
Patent Document 2: JP-A 2002-151272
Patent Document 3: WO 2005/043962 Pamphlet
Patent Document 4: WO 2004/043117 Pamphlet
Patent Document 5: WO 2005/107335 Pamphlet
Patent Document 6: WO 2004/105446 Pamphlet

DISCLOSURE OF THE INVENTION

Problems to be Solved by the Invention

The invention has been made under these circumstances and has for its object the provision of a charge-transporting varnish including an oxidized oligoaniline that exhibits high solubility in various types of organic solvents and also exhibits non-aggregation properties, thus being good at filterability.

Means for Solving the Problem

We made intensive studies in order to achieve the above object and found that a phenylamino-N,N'-diphenylquinonediimine derivative represented by the following formula (1) exhibits high solubility without aggregation in the varnish and thus, exhibits good filterability as selected from oligoaniline analogous compounds as an oxidized compound and that when formed as a thin film, high conductivity and good OLED characteristics are shown and such a derivative is suited as a conductive material or a hole injection material, thus accomplishing the invention.

More particularly, the invention provides:
1. A charge-transporting material consisting of a phenylamino-N,N'-diphenylquinonediimine derivative represented by the formula (1)

[Chemical Formula 1]

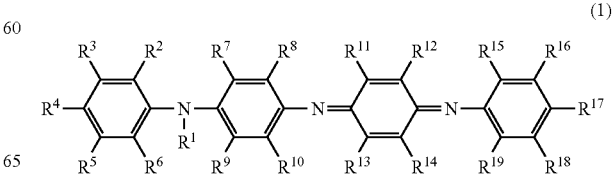

(wherein $R^1$ represents a hydrogen atom or a substituted or unsubstituted monovalent hydrocarbon group, $R^2$ to $R^{19}$ independently represent a hydrogen atom, a hydroxyl group, an amino group, a silanol group, a thiol group, a carboxyl group, a phosphoric acid group, a phosphate ester group, an ester group, a thioester group, an amide group, a nitro group, a substituted or unsubstituted monovalent hydrocarbon group, an organooxy group, an organoamino group, an organosilyl group, an organothio group, an acyl group, a sulfone group or a halogen atom);

2. A charge-transporting varnish including the charge-transporting material of 1;

3. The charge-transporting varnish of 2, wherein $R^1$ to $R^{19}$ are each a hydrogen atom;

4. The charge-transporting varnish of 2 or 3, wherein said varnish includes a 1,4-benzodioxanesulfonic acid compound represented by the formula (8), a 1,4-benzodioxane-sulfonic acid compound represented by the formula (9), a 1,4-benzodioxanesulfonic acid compound having repeating units represented by the formula (10), or a 1,4-benzodioxane-sulfonic acid compound having repeating units represented by the formula (11)

[Chemical Formula 2]

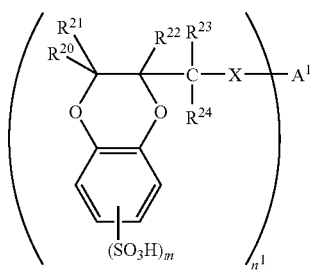

(8)

[wherein $R^{20}$ to $R^{24}$ independently represent a hydrogen atom, a substituted or unsubstituted monovalent hydrocarbon group or a halogen atom, X represents a single bond, O, S or NH, $A^1$ represents a hydrogen atom, a halogen atom (provided that X is a single bond), S (provided that X is a single bond), an S(O) group, an S(O$_2$) group, an N, Si, P or P(O) group unsubstituted or bonded with a substituent group, a substituted or unsubstituted hydrocarbon group, a 1,3,5-triazine group or a substituted or unsubstituted group represented by the following formula (12) or (13)

[Chemical Formula 3]

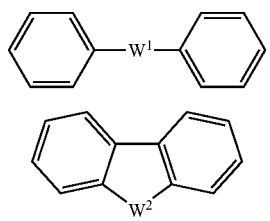

(12)

(13)

(wherein $W^1$ and $W^2$ independently represent an O, S, S(O) group, an S(O$_2$) group, or an N, Si, P or P(O) group unsubstituted or bonded with a substituent group), $n^1$ is an integer that is equal to the valence of $A^1$ and satisfies the relation of $1 \leq n^1$, and m is the number of sulfonic acid groups bonded to a benzene ring moiety of the 1,4-benzodioxane skeleton],

[Chemical Formula 4]

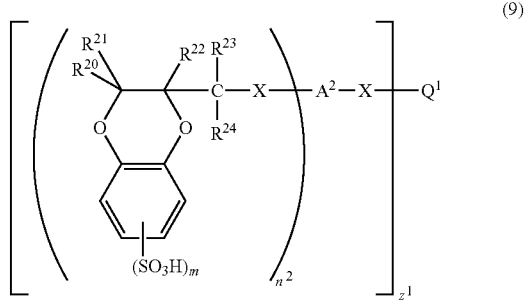

(9)

(wherein $R^{20}$ to $R^{24}$, X and m, respectively, have the same meanings as defined above, $A^2$ represents a substituted or unsubstituted, divalent or higher valent hydrocarbon group, a divalent or trivalent 1,3,5-triazine group or a substituted or unsubstituted group represented by the above-indicated formula (12) or (13), $Q^1$ represents a hydrogen atom, a halogen atom (provided that X is a single bond), S (provided that X is a single bond), an S(O) group, a S(O$_2$) group, an N, Si, P or P(O) group unsubstituted or bonded with a substituent group, a substituted or unsubstituted hydrocarbon group, a 1,3,5-triazine group or a substituted or unsubstituted group represented by the above-indicated formula (12) or (13), $n^2$ is an integer that is equal to (the valence of $A^2-1$) and satisfies the relation of $1 \leq n^2$, and $z^1$ is an integer that is equal to the valence of $Q^1$ and satisfies the relation of $1 \leq z^1$),

[Chemical Formula 5]

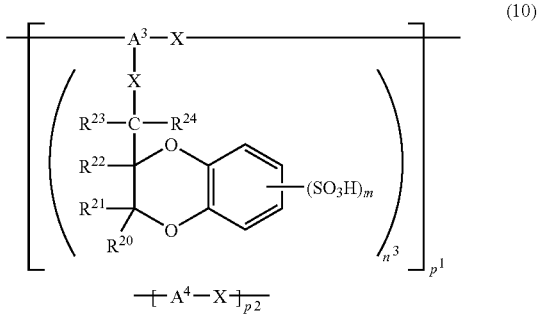

(10)

(wherein $R^{20}$ to $R^{24}$, X and m, respectively, have the same meanings as defined above, $A^3$ represents a substituted or unsubstituted, trivalent or higher valent hydrocarbon group, a trivalent 1,3,5-triazine group or a substituted or unsubstituted group represented by the above-indicated formula (12) or (13), $A^4$ represents a substituted or unsubstituted, divalent or higher valent hydrocarbon group, a divalent or trivalent 1,3,5-triazine group or a substituted or unsubstituted group represented by the above-indicated formula (12) or (13), $n^3$ is an integer that is equal to (the valence of $A^3-2$) and satisfies the relation of $1 \leq n^3$, $p^1$ is an integer satisfying the relation of $1 \leq p^1$, and $p^2$ is an integer satisfying the relation of $0 \leq p^2$ provided that $1 \leq p^1 + p^2 \leq 10000$ is satisfied), or

[Chemical Formula 6]

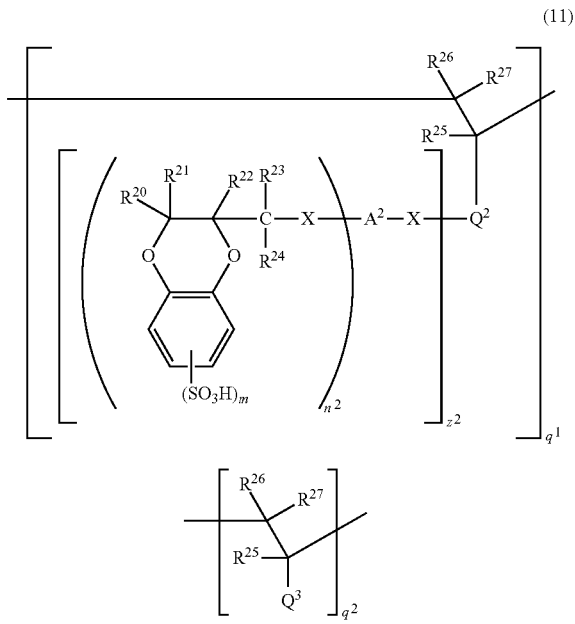

(11)

(wherein $R^{20}$ to $R^{24}$, $A^2$, X, m and $n^2$, respectively, have the same meanings as defined above, $R^{25}$ to $R^{27}$ independently represent a hydrogen atom, a substituted or unsubstituted monovalent hydrocarbon group or a halogen atom, $Q^2$ represents a substituted or unsubstituted, divalent or higher valent hydrocarbon group, a divalent or trivalent 1,3,5-triazine group or a substituted or unsubstituted group represented by the afore-indicated formula (12) or (13), $Q^3$ represents a substituted or unsubstituted hydrocarbon group, a 1,3,5-triazine group or a substituted or unsubstituted group represented by the afore-indicated formula (12) or (13), $z^2$ is an integer that is equal to (the valence of $Q^2$–1) and satisfies the relation of $1 \leq z^2$, $q^1$ is an integer satisfying the relation of $1 \leq q^1$ and $q^2$ is an integer satisfying the relation of $0 \leq q^2$ provided that $1 \leq q^1 + q^2 \leq 10000$);

5. The charge-transporting varnish of 2 or 3 including an arylsulfonic acid compound represented by the formula (14) or (15)

[Chemical Formula 7]

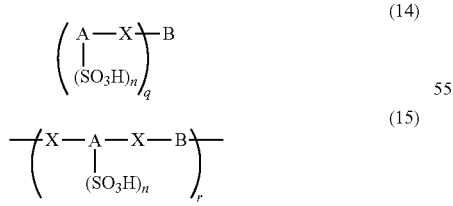

(14)

(15)

[wherein X represents O, S or NH, A represents X, or a naphthalene ring or an anthracene ring which may have a substituent other than an n number of $(SO_3H)$ groups, B represents a substituted or unsubstituted hydrocarbon group, a 1,3,5-triazine group, or a substituted or unsubstituted group represented by the following formula (12) or (13)

[Chemical Formula 8]

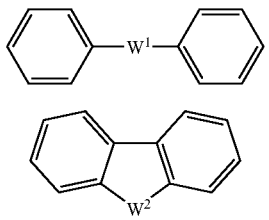

(12)

(13)

(wherein $W^1$ and $W^2$ independently represent O, S, an S(O) group, an $S(O_2)$ group or an N, Si, P or P(O) group unsubstituted or bonded with a substituent group), n is the number of sulfonic acid groups bonded with A and is an integer satisfying $1 \leq n \leq 4$, q indicates the number of bonds between B and X and is an integer satisfying $1 \leq q$, and r indicates the number of repeating units and is an integer of satisfying $1 \leq r$];

6. A charge-transporting thin film made by use of the charge-transporting varnish of any one of 2 to 5;

7. A charge-transporting thin film including the charge-transporting material of 1;

8. An organic electroluminescent device including the charge-transporting thin film of 6 or 7; and 9. A method for preparing a phenylamino-N,N'-diphenylquinonediimine derivative represented by the formula (1)

[Chemical Formula 12]

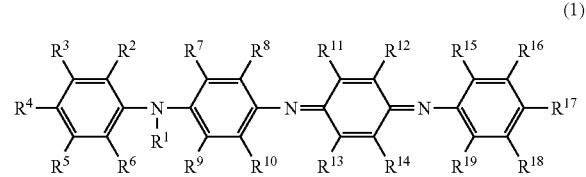

(1)

(wherein $R^1$ to $R^{19}$, respectively, have the same meanings as defined before), characterized by subjecting a 4-hydroxydiphenylamine compound represented by the formula (2) or (3)

[Chemical Formula 9]

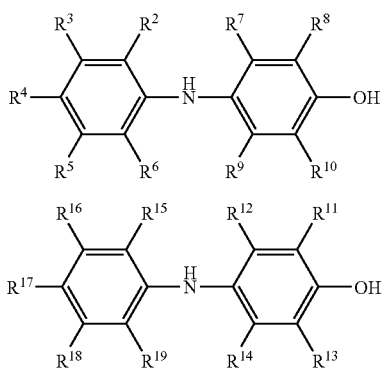

(2)

(3)

(wherein $R^2$ to $R^{19}$, respectively, have the same meanings as defined before) and a 4-aminodiphenylamine represented by the formula (4) or (5)

[Chemical Formula 10]

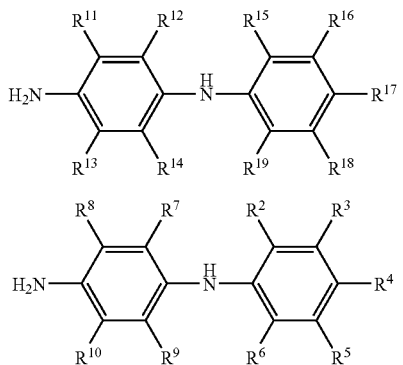

(wherein $R^2$ to $R^{19}$, respectively, have the same meanings as defined before) to reaction with each other in the presence of a titanium alkoxide catalyst to prepare a phenyltetraaniline compound represented by the formula (6)

[Chemical Formula 11]

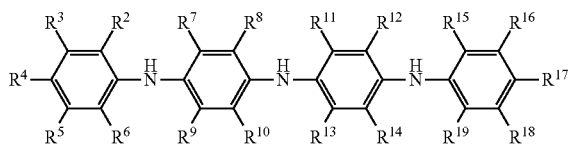

(wherein $R^2$ to $R^{19}$, respectively, have the same meanings as defined before), and further treating with an oxidizing agent.

Effects of the Invention

The phenylamino-N,N'-diphenylquinonediimine derivative that is a charge-transporting material present in the charge-transporting varnish of the invention shows high solubility and non-aggregation property and is thus good at filterability, along with a high synthesis yield. By utilizing this high solubility in organic solvents, the charge-transporting varnish can be prepared by using not only polar solvents, but also relatively low-polarity alcohol solvents, ether solvents, ester solvents or ketone solvents in combination. Additionally, liquid physical properties of the varnish can be controlled with ease.

The above-indicated derivatives have high crystallinity while rare as an oxidized oligoaniline compound, so that easy and high purification becomes possible by recrystallization operations. In this way, impurities can be eliminated. In addition, the varnish results in a complete homogeneous solution, so that a thin film can be formed without causing defects or irregularities to occur.

Further, irrespective of a small number of aniline repeating units, the above derivative exhibits high charge transportability when used in combination with electron accepting materials, so that there can be shown good OLED characteristics or PLED characteristics. In addition, when compared with reduced (leuco emeraldin type) oligoaniline analogous compounds, the derivative is able to develop functions thereof in case where baked within a short time or baked at low temperatures, or baked in an atmosphere of an inert gas such as nitrogen gas.

The organic solvent-based charge-transporting varnish that contains a phenylamino-N,N'-diphenylquinonediimine derivative having such characteristics as mentioned above as a charge-transporting material is applicable to uses as a capacitor electrode protecting film, a proton polymer cell, a solar cell and an antistatic film.

BEST MODE FOR CARRYING OUT THE INVENTION

Figure 1:
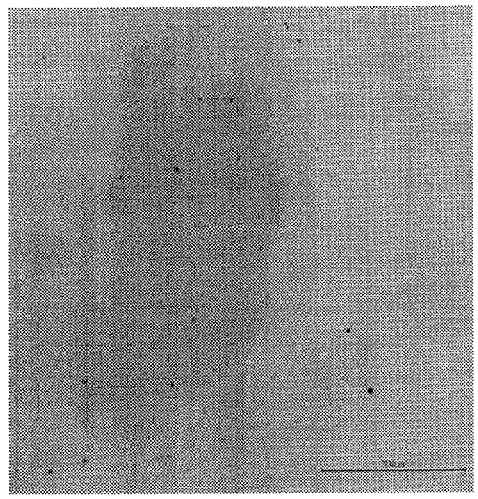
FIG. 1 is a laser confocal microphotograph (objective ×20 lenses) of a charge-transporting thin film obtained in Example 6.

The invention is now described in more detail.

The charge-transporting varnish of the invention includes as a charge-transporting material a phenylamino-N,N'-diphenylquinonediimine derivative represented by the formula (1). The phenylamino-N,N'-diphenylquinonediimine derivative represented by the formula (1) has charge transportability and can be favorably used as a charge-transporting material, especially as a hole-transporting material. It will be noted that charge transportability has the same meaning as electric conductivity. The charge-transporting varnish may have charge transportability in itself or a solid film obtained from the varnish may have charge transportability.

[Chemical Formula 13]

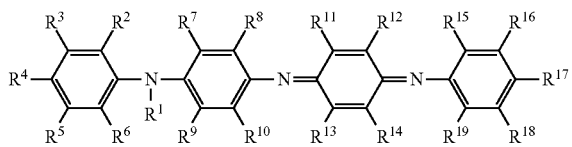

In the formula (1), $R^1$ represents a hydrogen atom or a substituted or unsubstituted monovalent hydrocarbon group.

The number of the carbon atoms in the monovalent hydrocarbon group is not limited and is generally in the range of 1 to 20, preferably 1 to 8.

Specific examples of the substituted or unsubstituted monovalent hydrocarbon group include: an alkyl group such as a methyl group, an ethyl group, a n-propyl group, an i-propyl group, a n-butyl group, an i-butyl group, a t-butyl group, a n-hexyl group, a n-octyl group, a 2-ethylhexyl group, a decyl group or the like; a cycloalkyl group such as a cyclopentyl group, a cyclohexyl group or the like; a bicycloalkyl group such as a bicylohexyl group or the like; an alkenyl group such as a vinyl group, a 1-propenyl group, a 2-propenyl group, an isopropenyl group, a 1-methyl-2-propenyl group, a 1 or 2 or 3-butenyl group, a hexenyl group or the like; an aryl group such as a phenyl group, a xylyl group, a tolyl group, a biphenyl group, a naphthyl group or the like; an aralkyl group such as a benzyl group, a phenylethyl group, a phenylcyclohexyl group or the like; and those monovalent groups mentioned above wherein part or all of the hydrogen atoms of the monovalent groups are substituted with a halogen atom, a hydroxyl group, an alkoxy group, a sulfonate group or the like.

Especially, it is preferred to use as $R^1$ a hydrogen atom, a methyl group or an ethyl group.

It will be noted that the term "unsubstituted" means that a hydrogen atom is bonded. Substituent groups may be mutually combined to provide a cyclic moiety.

$R^2$ to $R^{19}$ independently represent a hydrogen atom, a hydroxyl group, an amino group, a silanol group, a thiol group, a carboxyl group, a sulfonic acid group, a phosphoric acid group, a phosphate ester group, an ester group, a thioester group, an amide group, a nitro group, a substituted or unsubstituted monovalent hydrocarbon group, an organooxy group, an organoamino group, an organosilyl group, an organothio group, an acyl group, a sulfone group or a halogen atom.

Specific examples of the substituted or unsubstituted monovalent hydrocarbon group are similar to those mentioned above.

Specific examples of the organooxy group include an alkoxy group, an alkenyloxy group, an aryloxy group and the like. These alkyl groups, alkenyl groups and aryl group are similar to those exemplified as substituent groups mentioned above.

Specific examples of the organoamino group include: an alkylamino group such as a methylamino group, an ethylamino group, a propylamino group, a butylamino group, a pentylamino group, a hexylamino group, a heptylamino group, an octylamino group, a nonylamino group, a decylamino group, a laurylamino group or the like; a dialkylamino group such as a dimethylamino group, a diethylamino group, a dipropylamino group, a dibutylamino group, a dipentylamino group, a dihexylamino group, a diheptylamino group, a dioctylamino group, a dinonylamino group, a didecylamino group or the like; a dicycloalkylamino group such as a cyclohexylamino group or the like; and a morpholino group.

Specific examples of the organosilyl group include a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group and the like.

Specific examples of the organothio group include alkylthio groups such as a methylthio group, an ethylthio group, a propylthio group, a butylthio group, a pentylthio group, a hexylthio group, a heptylthio group, an octylthio group, a nonylthio group, a decylthio group, a laurylthio group and the like.

Specific examples of the acyl group include a formyl group, an acetyl group, a propionyl group, a butyryl group, an isobutyryl group, a valeryl group, an isovaleryl group, a benzoyl group and the like.

The number of carbon atoms of the monovalent hydrocarbon group, organooxy group, organoamino group, organoamino group, organosilyl group, organothio group and acyl group is not critical and is generally in the range of 1 to 20, preferably 1 to 8.

Of the above-mentioned substituent groups, a hydrogen atom, a substituted or unsubstituted organooxy group, an alkyl group and an organosilyl group are more preferred.

In the charge-transporting varnish of the invention, other type of charge-transporting material may be mixed with the phenylamino-N,N'-diphenylquinonediimine derivative represented by the formula (1) for use as a charge-transporting material.

Other type of charge-transporting material is not limited in type so far as a charge-transporting monomer, oligomer or polymer that can be uniformly dissolved or dispersed in a solvent is used. It is preferred to use an oligomer having a sequence of one type of conjugated unit or an oligomer having a combination of sequences of different types of conjugated units.

The conjugated unit is not limited to a specific one so far as there is used an atom, an aromatic ring or a conjugated group that is able to transport charges. Preferably, mention is made of a substituted or unsubstituted divalent to tetravalent aniline group, thiophene group, furan group, pyrrole group, ethynylene group, vinylene group, phenylene group, naphthalene group, oxadiazole group, quinoline group, silol group, silicon atom, pyridine group, phenylenevinylene group, fluorene group, carbazole group, triarylamine group, metal or metal-free phthalocyanine group, metal or metal-free porphyline group and the like. The conjugated chain formed by connection of conjugated units may contain a cyclic moiety.

The substituent groups independently represent hydrogen, a hydroxyl group, a halogen group, an amino group, a silanol group, a thiol group, a carboxyl group, a phosphoric acid group, a phosphate ester group, an ester group, a thioester group, an amide group, a nitro group, a monovalent hydrocarbon group, an organooxy group, an organoamino group, an organosilyl group, an organothio group, an acyl group, a sulfone group and the like, and these functional groups may be further substituted with any of the functional groups.

It will be noted specific examples of the monovalent hydrocarbon group, organooxy group, organoamino group, organosilyl group, organothio group and acyl group are similar to those mentioned above. In this connection, the number of carbon atoms of the respective substituent groups is not critical and is generally in the range of 1 to 20, preferably 1 to 8.

Preferred substituent groups include fluorine, a sulfone group, a substituted or unsubstituted organooxy group, an alkyl group or an organosilyl group.

For improving solubility, the molecular weight of a charge-transporting material is preferably at not larger than 5000 and is preferably not smaller than 200 so as to ensure low volatility and development of charge transportability. Materials that exhibit high solubility in at least one solvent are conveniently used and may have a number average molecular weight of 5000 to 500,000 if they exhibit high solubility in at least one solvent.

As stated above, although the charge-transporting varnish of the invention should include at least one type of charge-transporting material serving as an essential component of a charge-transporting system of the invention, an electron-accepting material is preferably added so as to improve charge transportability and film uniformity. The electron-accepting material has the same meaning as charge-accepting dopant material. It is preferred that these materials are completely dissolved in a solvent in the charge-transporting varnish.

The electron-accepting material (charge-accepting dopant material) is not limited in type so far as it is dissolved in at least one solvent and should preferably have high charge acceptability.

Specific examples of such an electron accepting dopant material include: inorganic strong acids such as hydrogen chloride, sulfuric acid, nitric acid, phosphoric acid and the like; Lewis acids such as aluminium (III) chloride ($AlCl_3$), titanium (IV) tetrachloride ($TiCl_4$), boron tribromide ($BBr_3$), boron trifluoride ether complex ($BF_3 \cdot OEt_3$), iron (III) chloride ($FeCl_3$), copper (II) chloride ($CuCl_2$), antimony (V) pentachloride ($SbCl_5$), arsenic (V) pentafluoride ($AsF_5$), phosphorus pentafluoride ($PF_5$), tris(4-bromophenyl)aluminium hexachloroantimonate (TBPAH) and the like: organic strong acids such as benzenesulfonic acid, tosylic acid, camphorsulfonic acid, hydroxybenzenesulfonic acid, 5-sulfosalicylic acid, dodecylbenzenesulfonic acid, polystyrenesulfonic acid, 1,4-benzodioxanedisulfonic acid derivatives indicated by the afore-indicated formulas (8) to (11) and described in WO 2005/000832 Pamphlet, arylsulfonic acid derivatives described in WO 2006/025342 Pamphlet, dinonylnaphthalenesulfonic acid derivatives described in JP-A 2005-108828, and naphthalenedisulfonic acid derivatives represented by the afore-indicated formulas (14) and (15) and described in WO 2006/025342 Pamphlet; and organic or inorganic oxidizing agents such as 7,7,8,8-tetracyanoquino-dimethane (TCNQ), 2,3-dichloro-5,6-dicyano-1,4-benzoquinone (DDQ), iodine and the like although not limited thereto.

Preferred charge-accepting dopant materials include organic strong acids such as 5-sulfosalicylic acid, dodecylbenzenesulfonic acid, polystyrenesulfonic acid, 1,4-benzodioxanedisulfonic acid derivatives represented by the afore-indicated formulas (8) to (11) and described in WO 2005/000832 Pamphlet, dinonylnaphthalenesulfonic acid derivatives described in JP-A 2005-108828, and naphthalenedisulfonic acid derivatives represented by the afore-indicated formulas (14) and (15) and described in WO 2006/025342 Pamphlet.

It will be noted that two or more of dopant materials may be used in combination so as to improve wettability to a substrate, form a highly flat film upon baking and impart physical properties such as solubility, a heat resistance, photosensitivity and the like.

The monovalent hydrocarbon groups and halogen atoms in the formulas (8) to (11) are similar to those mentioned hereinbefore. Preferred $R^{20}$ to $R^{24}$ independently represent a hydrogen atom, a methyl group, an ethyl group, an i-propyl group, a t-butyl group, a 2-ethylhexyl group, a fluorine atom, and a chlorine atom.

X is preferably O. It will be noted that the single bond means that atoms or atomic groups adjacent to X directly bond with each other.

$A^1$ and $Q^1$ are not limited so far as they are independently a hydrogen atom, a halogen atom (only in the case that X is a single bond), S (only in the case that X is a single bond), an S(O) group, an $S(O_2)$ group, an N, Si, P or P(O) group unsubstituted or bonded with a substituent group, an unsubstituted or substituted hydrocarbon group, a 1,3,5-triazine group, or a substituted or unsubstituted group represented by the afore-indicated formula (12) or (13). Especially, taking improvements in durability and charge transportability into consideration, it is preferred to use a hydrogen atom, a substituted or unsubstituted divalent or higher valent hydrocarbon group having at least one aromatic ring, a divalent or trivalent 1,3, 5-triazine group, a substituted or unsubstituted divalent diphenylsulfone group. Moreover, it is more preferred to use a hydrogen atom, a divalent or trivalent substituted or unsubstituted benzyl group, a divalent substituted or unsubstituted p-xylylene group, a divalent or trivalent substituted or unsubstituted naphthyl group, a divalent or trivalent 1,3,5-triazine group, a divalent substituted or unsubstituted diphenylsulfone group, a divalent to tetravalent perfluorobiphenyl group, a divalent substituted or unsubstituted 2,2-bis(hydroxypropoxy)phenyl)-propyl group, a substituted or unsubstituted polyvinylbenzyl group and the like.

$n^1$ indicates a valence of $A^1$ and is not limited provided that it is an integer satisfying $1 \leq n^1$.

m indicates the number of sulfonic acid groups bonded to the benzene ring moiety of the 1,4-benzodioxane skeleton and is not limited so far as $1 \leq m \leq 4$. However, m is preferably 1 or 2 in order to assure high electron acceptability and high solubility.

The substituted or unsubstituted hydrocarbon group in $A^2$, $A^3$, $A^4$, $Q^2$ and $Q^3$ is not limited and in order to improve durability and charge transportability, there is favorably used a hydrocarbon group containing one or more aromatic rings, e.g. an unsubstituted benzyl group, a substituted or unsubstituted p-xylylene group, a substituted or unsubstituted naphtyl group, a perfluorobiphenyl group, a 2,2-bis((hydroxypropoxy)phenyl)propyl group, a substituted or unsubstituted polyvinylbenzyl group or the like. These may be used as having a valence within a range defined by the respective groups.

The substituted or unsubstituted group represented by the afore-indicated formula (12) or (13) in $A^2$, $A^3$, $A^4$, $Q^2$ and $Q^3$ is not limited, and like $A^1$ and $Q^1$, it is preferred to use a diphenylsulfone group of a valence within a range defined by the respective groups.

$n^2$ is equal to a value of (valence of $A^2$ −1) and is not limited so far as it is an integer satisfying $1 \leq n^2$.

$n^3$ is equal to a value of (valence of $A^3$ −2) and is not limited so far as it is an integer satisfying $1 \leq n^3$.

$p^1$ is an integer satisfying $1 \leq p^1$, and $p^2$ is an integer satisfying $0 \leq p^2$ provided that the relation of $1 \leq p^1+p^2 \leq 10000$, preferably $1 \leq p^1+p^2 \leq 5000$, is satisfied.

$q^1$ is an integer satisfying $1 \leq q^1$ and $q^2$ is an integer satisfying $0 \leq q^2$ provided that the relation of $1 \leq q^1+q^2 \leq 10000$, preferably $1 \leq q^1+q^2 \leq 5000$, is satisfied.

$z^1$ is equal to the valance of $Q^1$ and is not limited as far as it is an integer satisfying $1 \leq z^1$.

$z^2$ is equal to a value of (valence of $Q^2$ −1) and is not limited as far as it is an integer satisfying $1 \leq z^2$.

Specific examples of the 1,4-benzodioxanesulfonic acid compound include oligomers of 1,4-benzodioxanesulfonic acid compounds (hereafter abbreviated as BDSO) and polymers of 1,4-benzodioxanesulfonic acid compound (hereinafter abbreviated as BDSP) represented by the following formulas, respectively, although not limited thereto.

[Chemical Formula 14]

BDSO-1

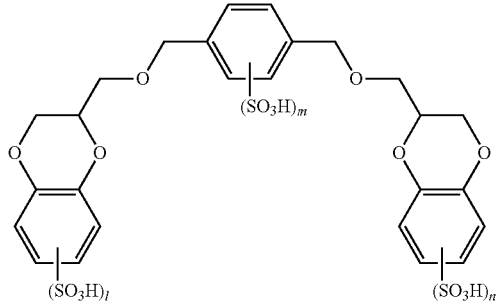

BDSO-2
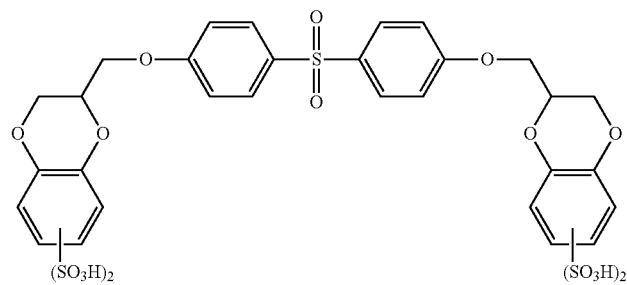
BDSO-3
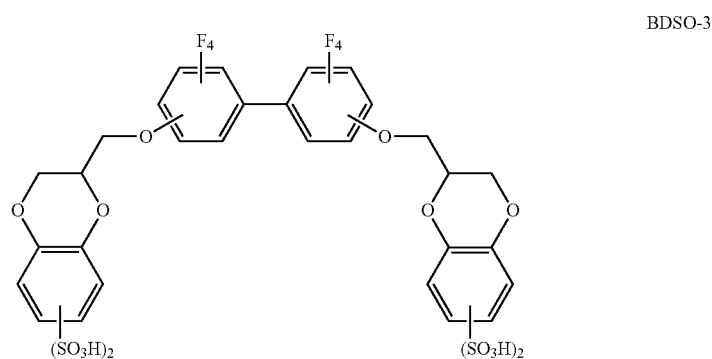
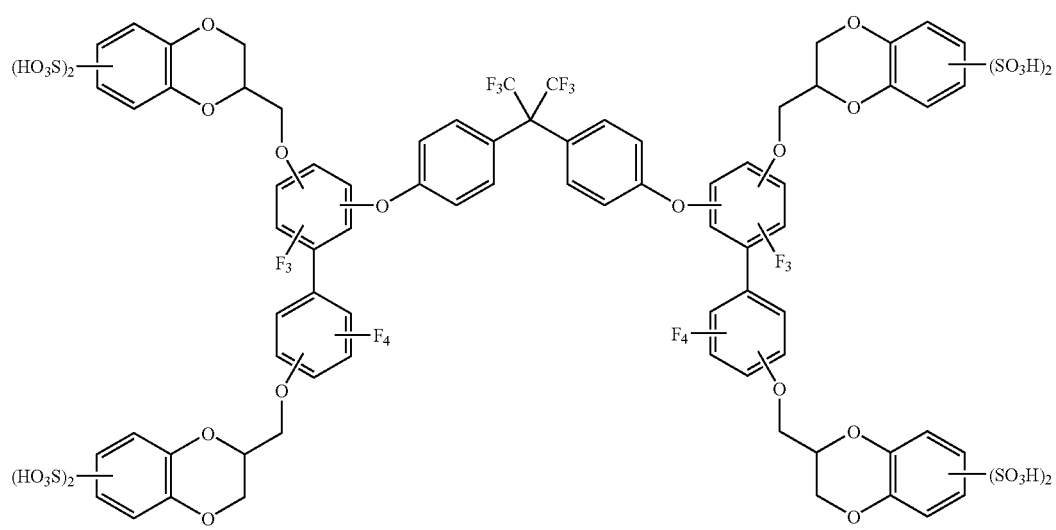
BDSO-4

[Chemical Formula 15]
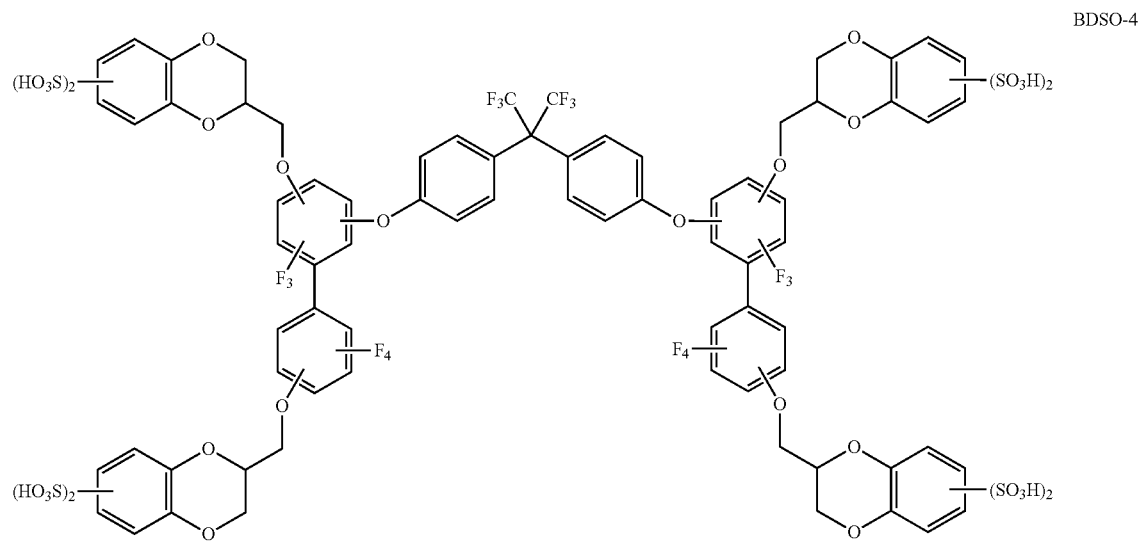
BDSO-4
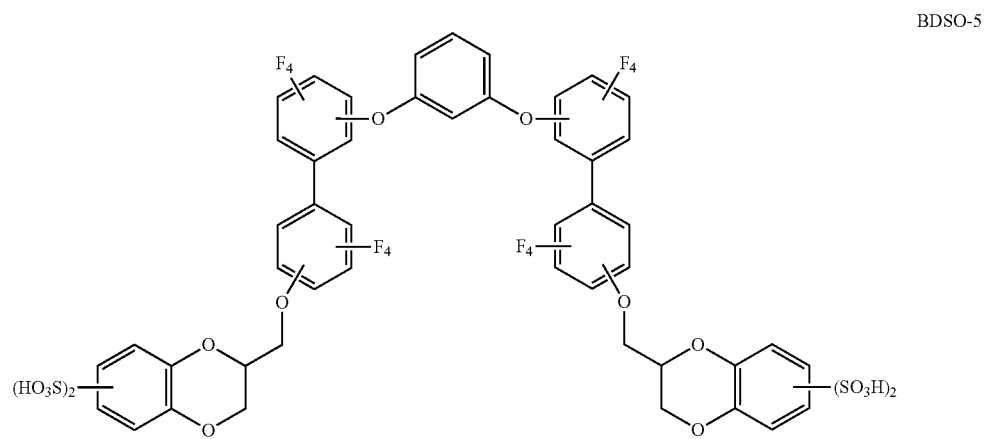
BDSO-5

-continued
BDSO-6
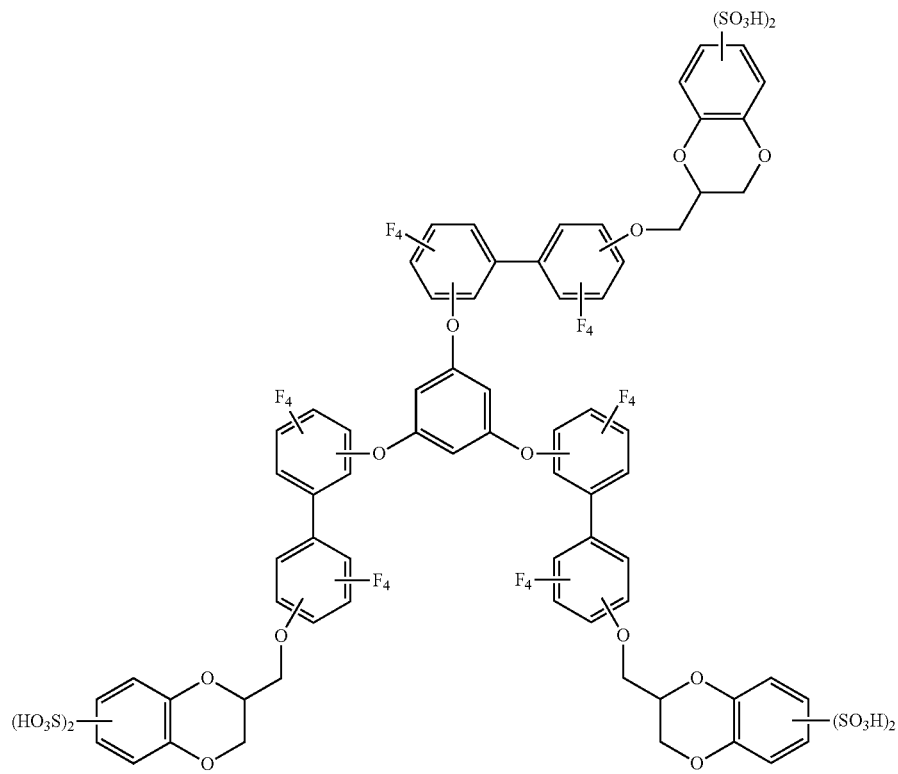
[Chemical formula 16]
BDSP-1
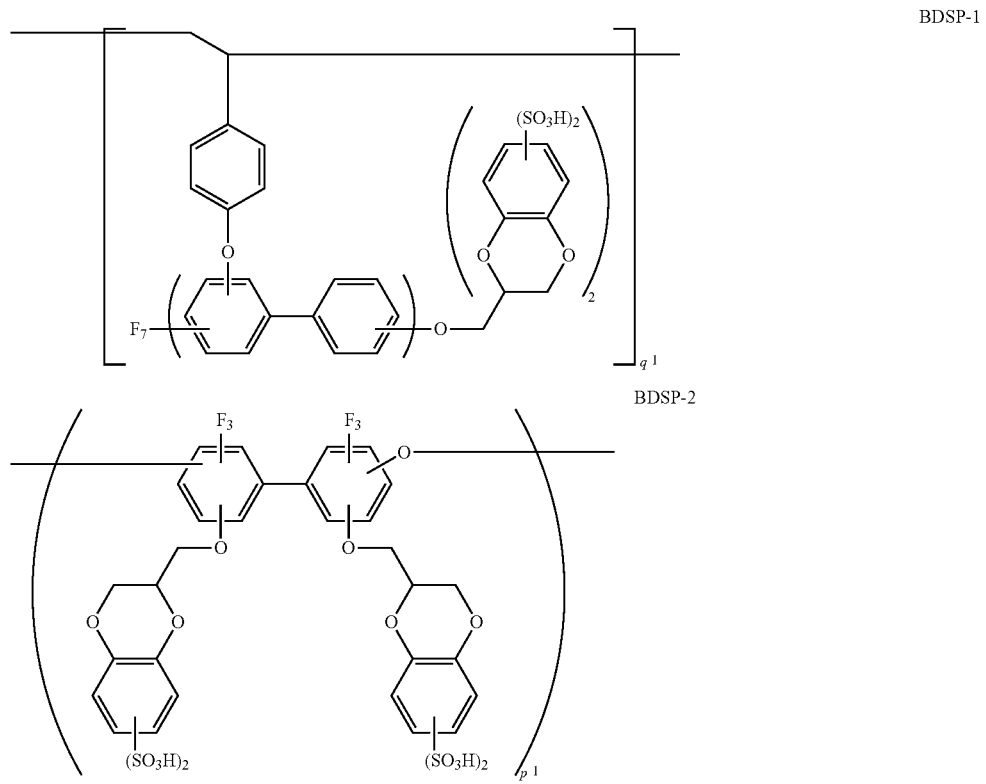
BDSP-2

In the formulas (14) and (15), specific examples of the substituents other than X and an (SO$_3$H) group include a hydroxyl group, an amino group, a silanol group, a thiol group, a carboxyl group, a phosphoric acid group, a phosphate ester group, an ester group, a thioester group, an amide group, a nitro group, a monovalent hydrocarbon group, an organooxy group, an organoamino group, an organosilyl group, an organothio group, an acyl group, a sulfone group, a halogen atom and the like although not limited thereto. Specific examples of these monovalent hydrocarbon group, organooxy group, organoamino group, organosilyl group, organothio group, acyl group and halogen atom are similar to those mentioned before.

It will be noted that the above-mentioned substituents may contain a cyclic moiety wherein substituents are mutually combined together.

X is preferably O.

B is not limited so far as it represents an unsubstituted or substituted hydrocarbon group, a 1,3,5-triazine group or an unsubstituted or substituted group represented by the aforeindicated formula (13) or (14) although not limited thereto. In this case, when taking improvements in durability and charge transportability into consideration, it is preferred to use as B a divalent and higher valent substituted or unsubstituted hydrocarbon group containing one or more aromatic rings, a divalent or trivalent 1,3,5-triazine group, or a substituted or unsubstituted divalent diphenylsulfone group. More specifically, there are preferably mentioned a divalent or trivalent substituted or unsubstituted benzyl group, a divalent substituted or unsubstituted p-xylylene group, a divalent or trivalent substituted or unsubstituted naphthyl group, a divalent or trivalent 1,3,5-triazine group, a divalent substituted or unsubstituted diphenylsulfone group, a divalent to tetravalent perfluorobiphenyl group, a divalent substituted or unsubstituted 2,2-bis((hydroxypropoxy)-phenyl)propyl group, and a substituted or unsubstituted polyvinylbenzyl group.

n is indicates the number of sulfonic acid groups bonded to A that represents an aryl skeleton and is not limited so far as 1≤n≤4. When imparting high electron acceptability and high solubility to the compound are taken into consideration, n is preferably 1 or 2.

q indicates the number of bonds between B and X and is not limited so far as it is an integer satisfying the relation of 1≤q. However, 2≤q is preferred.

r indicates the number of repeating units and is not limited so far as it is an integer satisfying 1≤r. However, 2≤r is preferred.

Specific examples of the arylsulfonic acid compound include oligomers of naphthalenedisulfonic acid compound (hereinafter abbreviated as NSO) represented by the following formulas although not limited thereto.

[Chemical Formula 17]

NSO-1

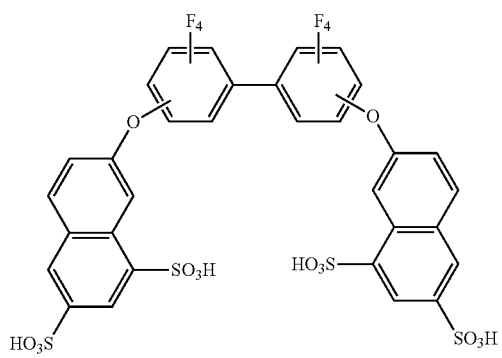

-continued

NSO-2

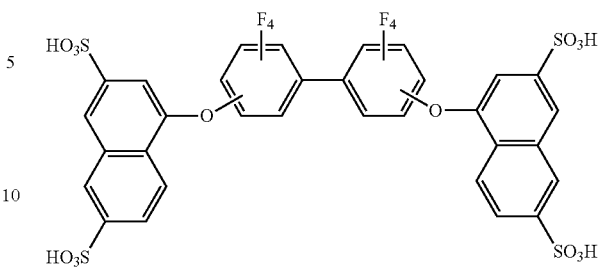

Solvents used to prepare a charge-transporting varnish include water and organic solvents such as methanol, N,N-dimethylformamide, N,N-dimethylacetamide, N-methylpyrrolidone, 1,3-dimethyl-2-imidazolidinone, dimethylsulfoxide, chloroform, toluene and the like. For the reasons set out above, organic solvents are preferred and especially, there are preferably used N,N-dimethylformamide, N,N-dimethylacetamide, N-methylpyrrolidone, and 1,3-dimethyl-2-imidazolidinone.

For the purposes of improving viscosity and wettability to a substrate and controlling the surface tension of a solvent, polarity and boiling point, there may be added to the solvent set out above a solvent imparting film flatness upon baking in an amount of 1 to 90 wt %, preferably 1 to 50 wt %, based on the total solvent used in the varnish.

Specific examples of such solvents include cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, 1,3-propanediol, hexylene glycol, butyl cellosolve, diethylene glycol diethyl ether, dipropylene glycol monomethyl ether, ethyl carbitol, methyl carbitol, diacetone alcohol, γ-butyrolactone, ethyl lactate, acetonitrile, ethanol, n-propanol, i-propanol, n-butanol, i-butanol, t-butanol, acetone, 2-butanone, carbon disulfide, nitromethane and the like although not limited thereto.

When the charge-transporting varnish is coated onto a substrate and a solvent is evaporated therefrom, a charge-transporting thin film can be formed on the substrate.

The coating methods are not limited and include a dipping method, a spin coating method, a transfer printing method, a roll coating method, a brushing method, an ink jet method, a spray method and the like.

The manner of evaporating a solvent is not limited and evaporation is made, for example, by using a hot plate or an oven in an appropriate atmosphere of air or an inert gas such as nitrogen or the like, or in vacuum. This allows a thin film having a uniform film-formed surface to be obtained.

The baking temperature is not limited so far as a solvent can be evaporated, and the baking is preferably effected at 40 to 250° C. In this case, the temperature may be changed by two or more stages so as to develop more uniform film-forming properties and allow a reaction to proceed on a substrate.

The charge-transporting thin film can also be formed by vacuum deposition of a phenylamino-N,N'-diphenylquinonediimine derivative represented by the formula (1).

The thickness of the charge-transporting thin film is not limited and where this film is used as a charge injection layer within an organic EL device, the thickness is preferably at 5 to 200 nm. The film thickness may be changed by a method wherein a solid concentration in the varnish is changed or by a method wherein an amount of the varnish on a substrate is changed upon coating.

The materials and the fabrication method used for the case where the charge-transporting varnish of the invention is used to make an OLED device may be those set out below although not limited thereto.

The electrode substrate used is preferably cleaned by preliminarily subjecting to liquid washing such as with a detergent, an alcohol, pure water or the like. With an anode substrate, for instance, it is preferred to carry out a surface treatment such as an ozone treatment, an oxygen-plasma treatment or the like immediately before use. However, if an anode material is mainly composed of an organic matter, the surface treatment may not be carried out.

Where a hole-transporting varnish is used for an OLED device, the following procedure may be used.

A hole-transporting varnish is coated onto an anode substrate and the solvent is evaporated by such a method set out hereinbefore, followed by baking to form a hole-transporting thin film on the electrode. This is introduced into a vacuum deposition apparatus, followed by successive vacuum deposition of a hole-transporting layer, an emission layer, an electron-transporting layer, an electron injection layer and a cathode metal, thereby providing an OLED device. In order to control an emission region, a carrier block layer may be provided between arbitrary layers.

The anode materials include transparent electrode materials, typical of which are an indium tin oxide (ITO), an indium zinc oxide (IZO) and the like. The transparent electrode whose surface is flattened is preferred. There may also be used polythiophene derivatives and polyaniline derivatives having high charge transportability.

The materials used for forming triarylamines such as a hole-transporting layer include a (triphenylamine) dimer derivative (TPD), (α-naphthyldiphenylamine) dimer (α-NPD), [(triphenylamine)dimer]spirodimer (Spiro-TAD) and the like, starburst amines 4,4',4"-tris[3-methylphenyl (phenyl)amino]-triphenylamine (m-MTDATA), 4,4',4"-tris [1-naphthyl(phenyl)-amino]triphenylamine (1-TNATA) and the like, and oligothiophenes such as 5,5"-bis-{4-[bis(4-methylphenyl)-amino]phenyl}-2,2':5',2"-terthiophene (BMA-3T) and the like.

The materials used to form an emission layer include tris (8-quinolinolate) aluminium (III) ($Alq_3$), bis(8-quinolinolate) zinc (II) ($Znq_2$), bis(2-methyl-8-quinolinolate(p-phenylphenolate) aluminium (III) (BAlq), 4,4'-bis(2,2-diphenylvinyl)biphenyl) (DPVBi) and the like. The emission layer may be formed by co-depositing an electron-transporting material or hole-transporting material and an light-emitting dopant.

The electron-transporting materials include $Alq_3$, BAlq, DPVBi, (2-(4-biphenyl)-5-(4-t-butylphenyl)-1,3,4-oxadiazole (PBD), a triazole derivative (TAZ), bathocuproine (BCP), a silol derivative and the like.

The light-emitting dopants include quinacridone, rubrene, coumarin 540, 4-(dicyanomethylene)-2-methyl-6-(p-dimethylaminostyryl)-4H-pyrane (DCM), tris(2-phenylpyridine) iridium (III) ($Ir(ppy)_3$), (1,10-phenanthroline)-tris(4,4,4-trifluoro-1-(2-thienyl)butane-1,3-dionato) europium (III) (Eu $(TTA)_3$-phen) and the like.

The materials for forming the carrier block layer include PBD, TAZ, BCP and the like.

The materials for forming the electron injection layer include lithium oxide ($Li_2O$), magnesium oxide (MgO), alumina ($Al_2O_3$), lithium fluoride (LiF), magnesium fluoride ($MgF_2$), strontium fluoride ($SrF_2$), Liq, Li(acac), lithium acetate, lithium benzoate and the like.

The cathode materials include aluminium, a magnesium-silver alloy, an aluminium-lithium alloy, lithium, sodium, potassium, cesium and the like.

Where an electron-transporting varnish is used for an OLED device, the following method is carried out.

The electron-transporting varnish is coated onto a cathode substrate to form an electron-transporting thin film, which is introduced into a vacuum deposition apparatus, followed by forming an electron-transporting layer, an emission layer, a hole-transporting layer and a hole injection layer by use of such materials as mentioned before, respectively, and forming a film of an anode material by sputtering to provide an OLED device.

Although the method of making a PLED device using the charge-transporting varnish of the invention is not limited, the following method may be used.

More particularly, instead of carrying out the vacuum deposition operations the hole-transporting layer, emission layer, electron-transporting layer and electron injection layer in the fabrication of the OLED device as set out above, a light-emitting charge-transporting polymer layer is formed, thereby enabling a PLED device including a charge-transporting thin film formed from the charge-transporting varnish of the invention to be fabricated.

Concretely speaking, a charge-transporting varnish (hole-transporting varnish) is coated onto an anode substrate to form a hole-transporting thin film by the procedure set out above, on which a light-emitting charge-transporting polymer layer is formed on top of the thin film, followed by vacuum deposition of a cathode electrode to provide a PLED device.

Alternatively, a charge-transporting varnish (electron-transporting varnish) may be coated onto a cathode substrate to form an electron-transporting thin film by the procedure set out above, on which a light-emitting charge-transporting polymer layer is formed on top of the thin film, followed by forming an anode electrode by sputtering, vacuum deposition, spin coating or the like method to provide a PLED device.

The materials for the cathode and anode are similar to those used for making the OLED device, and a similar cleaning treatment and surface treatment can be carried out.

For the formation of a light-emitting charge-transporting polymer layer, there is used a method wherein a solvent is added to a light-emitting charge-transporting polymer material with or without further addition of a light-emitting dopant to provide a solution or uniform dispersion thereof, followed by coating onto an electrode substrate on which a hole injection layer has been formed beforehand and evaporating the solvent to form a film of the polymer material.

The light-emitting charge-transporting polymer materials include polyfluorene derivatives such as poly(9,9-dialkylfluorene) (PDAF) and the like, polyphenylenevinylene derivatives such as poly(2-methoxy-5-(2'-ethylhexoxy)-1,4-phenylenevinylene) (MEH-PPV) and the like, polythiophene derivatives such as poly(3-alkylthiophene) (PAT) and the like, polyvinyl carbazole (PVCz) and the like.

The solvents include toluene, xylene, chloroform and the like, and stirring, stirring under heat, ultrasonic dispersion and the like methods are used for dissolution and uniform dispersion.

The coating method is not critical, for which mention is made of a ink jet method, a spraying method, a dipping method, a spin coating method, a transfer printing method, a roll coating method, a brushing method and the like. It will be noted that the coating is preferably carried out in an atmosphere of an inert gas such as nitrogen, argon or the like.

The solvent is evaporated in an inert gas or in vacuum by heating in an oven or with a hot plate.

Next, a process of preparing the phenylamino-N,N'-diphenylquinonediimine derivative represented by the afore-indicated formula (1) is illustrated.

The process of preparing the derivative represented by the formula (1) is set forth in document (Macromol. Rapid Commun., 20, 560-563 (1999)). In order to obtain phenyltrianiline and an oxidized product thereof in high purity by a short step, there is conveniently used a process wherein a phenyltrianiline compound is synthesized by application of a process described in document (Bull. Chem. Soc. Jpn., 67, 1749-1752 (1994)), followed by oxidation reaction. Moreover, an alkylation reaction is carried out so that a monovalent hydrocarbon group can be added to a free amino group.

More particularly, in a first step, a 4-hydroxydiphenylamine compound represented by the formula (2) or (3)

[Chemical Formula 18]

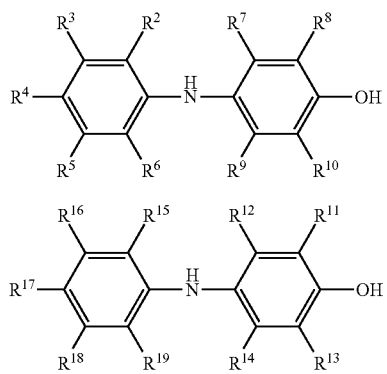

(wherein $R^2$ to $R^{19}$, respectively, have the same meanings as defined before)

and a 4-aminodiphenylamine represented by the formula (4) or (5)

[Chemical Formula 19]

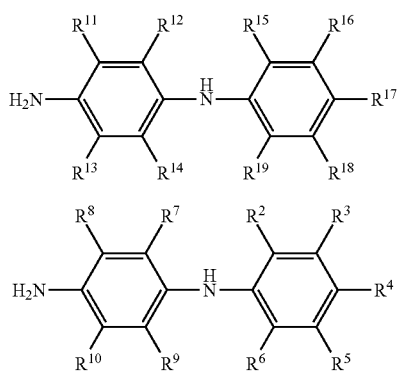

(wherein $R^2$ to $R^{19}$, respectively, have the same meanings as defined before)

are reacted in the presence of a titanium alkoxide catalyst to prepare a phenyltetraaniline compound represented by the formula (6)

[Chemical Formula 20]

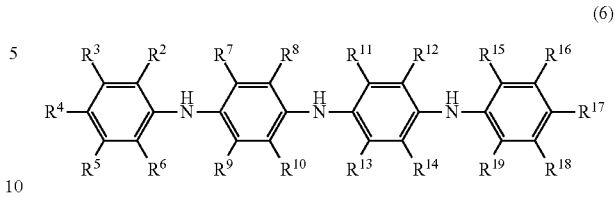

(6)

(wherein $R^2$ to $R^{19}$, respectively, have the same meanings as defined before).

In this case, in order to carry out the preparation in high purity and high yield, it is preferred that the 4-hydroxydiphenylamine compound represented by the formulas (2) and (3) and the 4-aminodiphenylamine compound represented by the formulas (4) and (5) are highly purified beforehand by purification operations such as of distillation under reduced pressure, recrystallization or the like.

The molar ratio between the compound (2) (or (3)) and the compound (4) (or (5)) in the reaction is preferably at 2:1 to 1:2, more preferably at 1.2:1 to 1:1.2, in order to suppress side reactions and the residue of unreacted starting materials.

The catalyst is a titanium alkoxide and preferably includes Ti(O-n-Bu)$_3$(OC$_6$H$_4$CH$_3$), Ti(O-n-Bu)$_4$, and Ti(O-n-Pr)$_4$, of which Ti(O-n-Bu)$_3$(OC$_6$H$_4$CH$_3$) is more preferred.

The amount of the catalyst is preferably at 1 to 5 times by mole, more preferably 1.2 to 3.0 times by mole, relative to the compound (2) or (3).

The reaction solvent is not limited as far as it does not take part in the reaction and preferably includes a solvent of low polarity having a boiling point of not lower than about 70° C., e.g. toluene, xylene, chlorobenzene, dichlorobenzene, dichloroethane or the like, of which toluene or xylene are more preferred.

Subsequently, in a second step, the phenyltetraaniline compound (6) prepared above is treated with an oxidizing agent to prepare a phenylamino-N,N'-diphenylquinonediimine derivative represented by the following formula (7).

[Chemical Formula 21]

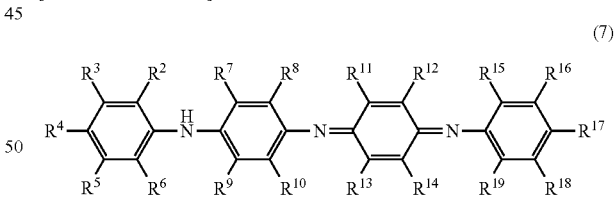

(7)

(wherein $R^2$ to $R^{19}$, respectively, have the same meanings as defined before).

In this case, although the oxidizing agent is not limited in type so far as it allows an oxidation reaction to proceed thereby enabling the formation of a quinoid structure, it is favorable to use an inorganic oxidizing agent such as silver(I) oxide, iron(III) chloride, iron(III) sulfate or the like, oxygen or air, of which silver(I) oxide is preferred from the standpoint that the reaction is allowed to proceed completely and a purification treatment after the reaction is easy.

The amount of an oxidizing agent, especially silver(I) oxide, is favorably at 1.5 to 5 times by mole relative to the phenyltrianiline compound (6) and is preferably at 1.7 to 3.0 times by mole so as to suppress adsorption and side reactions of the starting materials and an intended substance and cause the reaction to proceed completely.

The reaction solvent is not limited in type so far as it is able to dissolve starting materials and includes tetrahydrofuran (THF), dioxane, chloroform, 1,2-dichloroethane, dichloromethane, acetonitrile, acetic acid, ethyl acetate, acetone, diethyl ether, diisopropyl ether, dimethoxyethane, dimethylformamide, dimethylacetamide, 1,3-dimethyl-2-imidazolidinone, N-methylpyrrolidone, dimethylsulfoxide, toluene, xylene or the like, of which THF and dioxane are preferred.

The reaction temperature is not limited so far as it allows the oxidation reaction to proceed and is conveniently at 0 to 50° C.

Upon completion of the reaction, it should be confirmed by appropriate means such as of HPLC, TLC or the like that the oxidation reaction proceeds until an intended product is formed, and the reaction is preferably stopped at the time when the intended product is formed at the highest ratio upon comparison with side products and starting materials. The reaction time generally ranges from 20 minutes to about 3 hours.

After completion of the reaction, purification is feasible through operations such as of celite filtration, reduced pressure concentration, recrystallization or the like.

Further, an electrophilic reagent may be acted on the compound of the above formula (7) in the presence or absence of a catalyst, thereby introducing a monovalent hydrocarbon group on the amino group.

EXAMPLES

Synthetic Examples, Examples and Comparative Examples are shown below to more particularly describe the invention, and the invention should not be construed as limited to the following examples. Measuring apparatuses of NMR, MS and UV-VIS spectra are those indicated below.

[1] NMR
    Apparatus: ECX-300, made by JEOL Ltd.
    Solvent for measurement: dimethylsulfoxide-d6, made by Junsei Chemical Co., Ltd.
[2] MS
    Apparatus (MALDI-TOF): Voyager-DE ™ PRO, made by Applied Biosystems
    Apparatus (FAB): JMS-700T, made by JEOL Ltd.
[3] UV-VIS
    Apparatus: UV-3100PC, made by Shimadzu Corporation Synthetic Example 1

Synthesis of Oxidized Phenyltrianiline

According to the following procedure, oxidized phenyltrianiline (hereinafter abbreviated as ox-PTrA) was prepared through phenyltrianiline (hereinafter abbreviated as PTrA) prepared by use of 4-hydroxydiphenylamine (hereinafter abbreviated as HDPA) and 4-aminodiphenylamine (hereinafter abbreviated as ADPA).

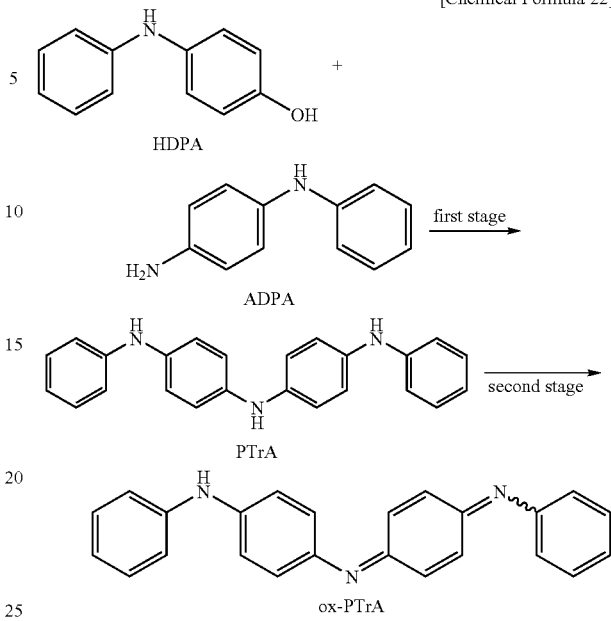

[Chemical Formula 22]

[1] First Step

HDPA (made by Tokyo Kasei Kogyou Co., Ltd.) and ADPA (made by Tokyo Kasei Kogyou Co., Ltd.) were, respectively, subjected to reduced distillation under heating (HDPA: 187 to 188° C., ADPA: 185 to 188° C.) by use of a vacuum pump and allowed to cool and the resulting crystals were used for the reaction.

Dehydrated toluene (550 ml) was added to 50.36 g (0.2719 mol) of HDPA and 50.04 g (0.2716 mol) of ADPA, followed by dissolution by heating to 90° C.

On the other hand, a mixed solution of 138.80 g (0.4078 mol) of Ti(O-n-Bu)$_4$ (made by Kanto Chemical Co. Inc.) and 61.26 g (0.4079 mol) of p-tolyl acetate (made by Kanto Chemical Co. Inc.) was stirred under a reduced pressure (<10 Pa) at 65° C. for 2.5 hours by use of an evaporator thereby preparing Ti(O-n-Bu)$_3$(O—C$_6$H$_4$CH$_3$) serving as a reaction catalyst while removing the resulting butyl acetate.

The thus obtained Ti catalyst was dissolved by addition of 200 ml of toluene thereto and the resulting solution was charged into the above reaction system that was kept at 90° C. After the charge, the reaction solution was heated up to 100° C. and stirred for 18 hours as it is. After allowing to cool down to room temperature, the reaction solution was filtered and the resulting silver crystals were washed successively with 700 ml of toluene and 300 ml of diethyl ether, followed by drying under reduced pressure to obtain 85.44 g (0.2431 mol, yield of 90%) of crude PTrA.

Two liters of dioxane and 8 g of activated carbon were added to 85.44 g of the crude PTrA and stirred under heating in an oil bath at 100° C. to dissolve the crude PTrA, followed by celite filtration under heating conditions. To the resulting filtrate, 500 ml of toluene was added and cooled down to room temperature. The resulting crystals were collected by filtration and successively washed three times with 200 ml of toluene and once with 200 ml of diethyl ether, followed by drying under reduced pressure to obtain 70.88 g (0.2017 mol, recrystallization yield of 83%, total yield of 74%) of light purple crystals of PTrA.

The results of measurement of $^1$H-NMR spectra of the thus obtained PTrA are shown below.

¹H-NMR (300 MHz, DMSO-d6): δ 7.78 (2H, s, NH), 7.68 (1H, s, NH), 7.15 (4H, dd, Ar—H), 6.85-7.05 (12H, m, Ar—H), 6.68 (2H, dd, Ar—H)

[2] Second Step

To 20.00 g (56.91 mmols) of PTrA obtained in the first step, 400 ml of THF was added, followed by stirring at room temperature for dissolution. To the resulting light purple transparent solution, 26.38 g (113.8 mmols) of silver(I) oxide (made by Kanto Chemical Co., Inc.) was added and stirred at room temperature for 50 minutes. The reaction solution was subjected to celite filtration and washed with THF, and a combined filtrate was concentrated to dryness under reduced pressure to obtain crude ox-PTrA. To the thus obtained crude ox-PTrA, 500 ml of toluene was added and heated to 100° C. for dissolution, to which 200 ml of hexane was added, followed by allowing to cool down to room temperature under stirring. The resulting crystals were collected by filtration and successively washed with a mixed solvent of toluene and hexane (1:1) and also with hexane, each cooled in an ice bath, followed by drying under reduced pressure to obtain 18.10 g (51.80 mmols), yield of 91%) of red crystals of ox-PTrA.

The results of measurements of ¹H-NMR spectra and MS spectra of the thus obtained ox-PTrA are shown below.

¹H-NMR (300 MHz, DMSO-d6): δ 6.7-7.5 (18H, m, Ar—H), 5.83 and 5.81 (1H, s, NH) (a mixture of E isomer and Z isomer).

MS (MALDI-TOF+): 350 [M+H]⁺

Reference 1

To 99.6 mg (0.283 mmol) of PTrA obtained in the first step of Synthetic Example 1, 10 ml of THF was added and stirred at room temperature for dissolution. To the resulting light purple transparent solution, 80.4 mg (0.347 mmol, i.e. about 1.2 equivalents relative to the starting PTrA) was added and stirred at room temperature. At the time when the stirring was made at room temperature for 15 minutes, TLC (developing solvent: chloroform:ethyl acetate=9:1) was used to follow up the reaction, revealing that PTrA was left at about 30% and no change was found after stirring at room temperature for 50 minutes. Moreover, 54.5 mg (0.235 mmol, i.e. 0.8 equivalents relative to the starting PTrA) was added to and stirred at room temperature for 80 minutes, whereupon it was confirmed that the starting materials disappeared.

From the above results, it will be seen that in order to prepare the intended compound, i.e. to form one quinoid structure from the starting oligoaniline (with the oxidation of PTrA, only one quinoid structure can be formed), the use of an equivalent to a slight excess (about 1.2 equivalents) of silver (I) oxide is not satisfactory.

Comparative Synthetic Example 1

Synthesis of Oxidized Phenyltetraaniline

Phenyltetraaniline (hereinafter abbreviated as PTA) was synthesized according to the procedure described in WO 2006/006459 Pamphlet. When THF was used as a solvent in the same manner as in the synthesis of ox-PTrA, starting PTA did not dissolve therein, for which dioxane was used and heated to 100° C. so as to dissolve PTA, followed by the reaction set out below.

To 4.05 g (9.15 mmols) of PTA, 200 ml of dioxane was added and was heated in an oil bath at 100° C. for dissolution, followed by further addition of 4.24 g (18.3 mmols) of silver (I) oxide and stirring in an oil bath at 100° C. for 30 minutes. The reaction solution was subjected to heating celite filtration and the resulting filtrate was concentrated to dryness to obtain 848 mg of a purple powder (yield: 21%). The thus formed oxidized PTA was low in solubility and the solid was left on the celite, thereby lowering the yield. Recrystallization of the thus obtained powder was not possible, so that it could not be possible to increase purity. The results of measurement of MS of the powder are shown below.

MS (FAB+): 440 [M(ox-PTA)]⁺, 441 [M(ox-PTA)+H]⁺, 442 [M(PTA)]⁺, 443 [M(PTA)+H]⁺

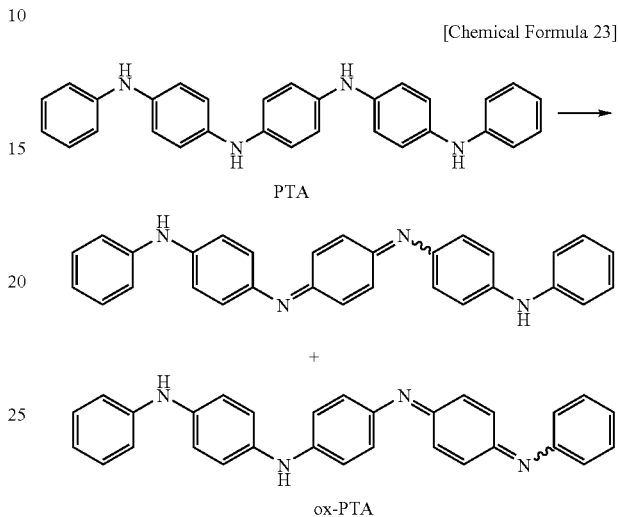

[Chemical Formula 23]

ox-PTA is worse in synthetic yield than ox-PTrA because of lower solubility and higher aggregation property. In addition, it will be seen that the purity is low because of the low crystallinity and large amounts of impure ingredients. It will be noted that as to ox-PTA, the existence of two types of isomers having different quinoid moieties after oxidation reaction using PTA as a starting material is shown in literature (Synthetic Metals, 84, 65-66 (1997)).

Comparative Synthetic Example 2

Synthesis of Oxidized Phenylpentaaniline

Phenylpentaaniline (hereinafter abbreviated as PPA) was synthesized according to the procedure described in document (Bull. Chem. Soc. Jpn., 67, 1749-1752 (1994)). Next, the oxidation reaction of PPA was attempted wherein THF was used as a solvent as in the case of synthesis of ox-PTrA whereupon starting PPA did not dissolve and dioxane was used and heated to 100° C. to dissolve PPA, followed by the following reaction.

To 2.03 g (3.80 mmols) of PPA, 250 ml of dioxane was added and heated in an oil bath at 100° C. for dissolution, to which 1.76 g (7.61 mmols) of silver(I) oxide was added to and stirred in an oil bath for 30 minutes. After allowing to cool, the reaction solution was subjected to celite filtration and the resulting filtrate was concentrated to dryness to obtain 1.97 g of a purple powder (yield of 97%). The thus obtained powder could not be recrystallized and thus, purity could not be increased. The results of measurement of MS of the powder are shown below.

MS (FAB+): 530 [M(ox²-PPA)+H]⁺, 531 [M(ox-PPA)]⁺, 532 [M(ox-PPA)+H]⁺, 533 [M(PPA)]⁺, 534 [M(PPA)+H]⁺

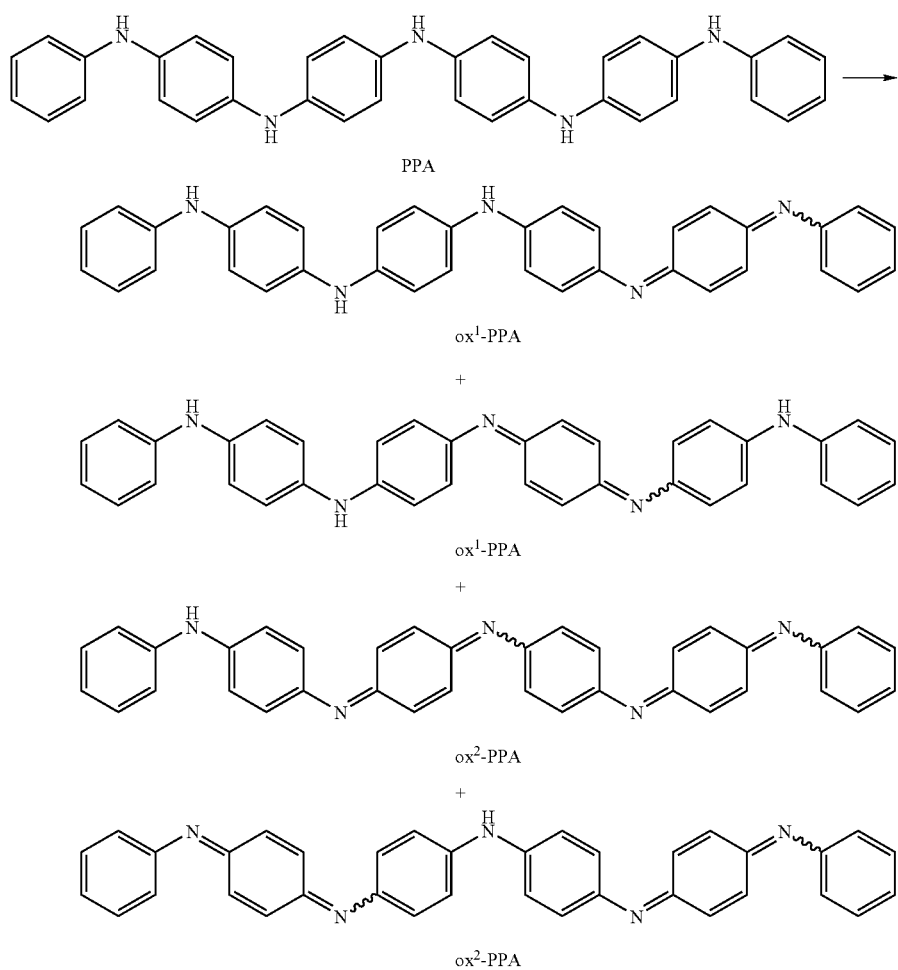

[Chemical Formula 24]

It will be seen that the oxidized PPA is lower in crystallinity and is also lower in purity than ox-PTrA because of large amounts of impure ingredients.

The mixture of the thus obtained oxidized PPA's (ox¹-PPA and ox²-PPA) is referred to hereinafter as ox-PPA. Upon calculation of moles, a mono-oxidized (ox¹-PPA) structure is used.

Example 1

Charge-Transporting Varnish

To a mixture of 100 mg (0.286 mmol) of ox-PTrA obtained in Synthetic Example 1 and 218 mg (0.859 mmol) of 5-sulfosalicylic acid dihydrate, 1.79 ml of DMAc was added, followed by dissolution under stirring at room temperature. To the solution, 5.31 ml of cyclohexanol melted by heating up to 50° C. was added and stirred to obtain greenish black transparent solution. The thus obtained solution was filtered through a PTFE filter (MX-13P with a diameter of 13 mm, made by Showa Denko K.K.) having a pore size of 0.2 μm, whereupon filtration was possible without clogging to obtain a greenish black transparent charge-transporting varnish. From this result, it will be seen that ox-PTrA has good solubility in a solvent (cyclohexanol/DMAc (3:1)) and good filterability. When the thus obtained charge-transporting varnish was stored for one day at −25° C., no solid precipitation was found.

Example 2

Charge-Transporting Varnish

The greenish black transparent solution obtained in Example 1 was provided as a charge-transporting varnish without filtration with the PTFE filter.

Comparative Example 1

Charge-Transporting Varnish

To a mixture of 100 mg (0.227 mmol) of ox-PTA obtained in Comparative Synthetic Example 1 and 231 mg (0.908 mmol) of 5-sulfosalicylic acid dihydrate, 1.86 ml of DMAc was added and stirred at room temperature, whereupon solids were left without complete dissolution. To the mixture, 5.51 ml of cyclohexanol melted by heating up to 50° C. was added and stirred to obtain a greenish black suspension. The thus obtained suspension was filtered through a TFE filter having a pore size of 0.2 μm, revealing that clogging occurred at the time when about 0.5 ml was filtered and filtration of the entire volume was not possible. A greenish black transparent charge-transporting varnish was obtained as a filtrate. The thus obtained charge transporting varnish was stored for one day at −25° C., whereupon no solid precipitation was observed. It will be seen that ox-PPA is lower in solubility and has a larger content of insoluble particles when compared with ox-PTrA.

Comparative Example 2

Charge-Transporting Varnish

To a mixture of 100 mg (0.188 mmol) of ox-PPA obtained in Comparative Synthetic Example 2 and 239 mg (0.940 mmol) of 5-sulfosalicylic acid dihydrate, 1.90 ml of DMAc was added and stirred at room temperature, whereupon a small amount of solids was left and thus, was not completely dissolved. To the mixture, 5.51 ml of cyclohexanol melted by heating up to 50° C. was added and stirred to obtain a greenish black solution containing a small amount of insoluble matters. The resulting solution was filtered through a PTFE filter having a pore size of 0.2 μm, whereupon clogging occurred at the time when about 0.5 ml was filtered and thus, filtration of the entire volume could not be possible. A greenish black transparent charge-transporting varnish was obtained as a filtrate. When the thus obtained charge-transporting varnish was stored for one day at −25° C., solids precipitated therefrom. When the varnish was heated to about 50° C., re-dissolution took place. It will be seen that ox-PPA is lower in solubility and contains a larger amount of insoluble particles when compared with ox-PTrA.

Comparative Example 3

Charge-Transporting Varnish

To a mixture of 100 mg (0.226 mmol) of reduced phenyltetraaniline (PTA) and 230 mg (0.904 mmol) of 5-sulfosalicylic acid dihydrate, 1.87 ml of DMAc was added and stirred at room temperature, to which 5.53 ml of cyclohexanol melted by heating up to 50° C. was added and stirred. The resulting light green transparent solution was filtered through a PTFE filter having a pore size of 0.2 μm, whereupon the filtration was possible without clogging thereby obtaining a light green transparent charge-transporting varnish.

Comparative Example 4

Charge-Transporting Varnish

The greenish black suspension obtained in Comparative Example 1 was provided as a charge-transporting varnish as it is without filtration with the PTFE filter.

Comparative Example 5

Charge-Transporting Varnish

The greenish black solution obtained in Comparative Example 2 was provided as a charge-transporting varnish as it is without filtration with the PTFE filter.

Examples 3 to 5

Charge-Transporting Thin Films

The varnish obtained in Example 1 was spin coated onto an ITO substrate which had been subjected to ozone cleaning for 40 minutes up to immediately before the coating and baked in air under different conditions indicated in Table 1 to form charge-transporting thin films (hole-transporting thin films). The thus obtained charge transporting thin films were made of a uniform amorphous solid.

Example 6

Charge-Transporting Thin Film

The varnish obtained in Example 2 was spin coated onto an ITO substrate which had been subjected to ozone cleaning for 40 minutes up to immediately before the coating and baked in air under conditions indicated in Table 1 to form a charge-transporting thin film (hole-transporting thin film). The thus obtained charge transporting thin film was made of a uniform amorphous solid as is particularly shown in FIG. 1.

Example 7

Charge-Transporting Thin Film

The varnish obtained in Example 1 was spin coated, in an atmosphere of nitrogen (with an oxygen concentration of 10 ppm or below), onto an ITO substrate which had been subjected to ozone cleaning for 40 minutes up to immediately before the coating and baked under conditions indicated in Table 1 to form a charge-transporting thin film. The thus obtained charge-transporting thin film was made of a uniform amorphous solid.

Comparative Example 6

Charge-Transporting Thin Film

The varnish obtained in Comparative Example 1 was spin coated onto an ITO substrate which had been subjected to ozone cleaning for 40 minutes up to immediately before the coating and baked in air under conditions indicated in Table 1 to form a charge-transporting thin film (hole-transporting thin film). The thus obtained charge-transporting thin film was made of a uniform amorphous solid.

Comparative Example 7

Charge-Transporting Thin Film

The varnish obtained in Comparative Example 2 was spin coated onto an ITO substrate which had been subjected to ozone cleaning for 40 minutes up to immediately before the coating and baked in air under conditions indicated in Table 1 to form a charge-transporting thin film (hole-transporting thin film). The thus obtained charge-transporting thin film was made of a uniform amorphous solid.

Comparative Examples 8 to 10

Charge-Transporting Thin Films

The varnish obtained in Comparative Example 3 was spin coated onto an ITO substrate which had been subjected to ozone cleaning for 40 minutes up to immediately before the coating and baked in air under different conditions indicated in Table 1 to form charge-transporting thin films (hole-transporting thin films). The thus obtained charge-transporting thin films were made of a uniform amorphous solid.

Comparative Example 11

Charge-Transporting Thin Film

Figure 2:
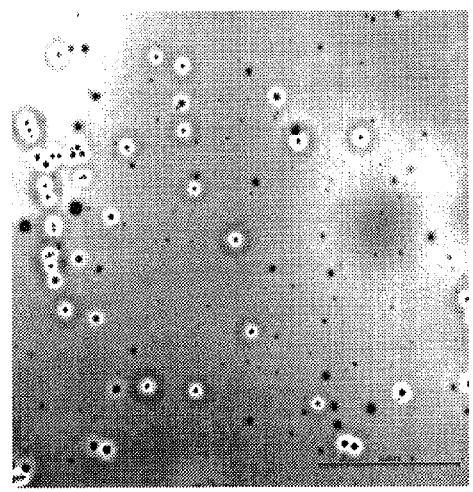
FIG. 2 is a laser confocal microphotograph (objective ×20 lenses) of a charge-transporting thin film obtained in Comparative Example 11.

The varnish obtained in Comparative Example 4 was spin coated onto an ITO substrate which had been subjected to ozone cleaning for 40 minutes up to immediately before the coating and baked in air under conditions indicated in Table 1 to form a charge-transporting thin film (hole-transporting thin film). The thus obtained charge-transporting thin film was great in irregularity as shown in FIG. 2 and no measurement of film thickness was possible.

Comparative Example 12

Charge-Transporting Thin Film

Figure 3:
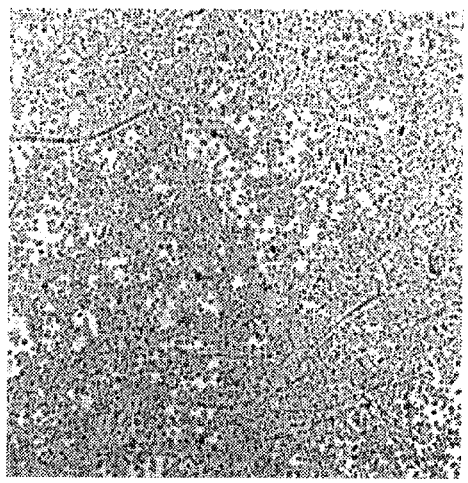
FIG. 3 is a laser confocal microphotograph (objective ×20 lenses) of a charge-transporting thin film obtained in Comparative Example 12.

The varnish obtained in Comparative Example 5 was spin coated onto an ITO substrate which had been subjected to ozone cleaning for 40 minutes up to immediately before the coating and baked in air under conditions indicated in Table 1 to form a charge-transporting thin film (hole-transporting thin film). The thus obtained charge-transporting thin film was great in irregularity as shown in FIG. 3 and no measurement of film thickness was possible.

The thickness and ionization potential (hereinafter abbreviated as Ip) of the thin films obtained in Examples 3 to 7 and Comparative Examples 6 to 12 are shown in Table 1. The viscosity of the employed varnishes is also shown in Table 1. It will be noted that Ip was measured by use of a photoelectronic spectrometer AC-2, made by Riken keiki Co., Ltd. The viscosity was measured at 25° C. by use of an E-type viscometer, made by Toki Sangyo Co., Ltd. The film thickness was measured by use of Surfcoder ET-4000A, made by Kosaka laboratory Ltd.

TABLE 1

| | Kind of varnish | Solid concentration (wt %) | Varnish viscosity [mPa · s] | Baking conditions | Film thickness [nm] | Ip [eV] |
|---|---|---|---|---|---|---|
| Example 3 | Example 1 | 4.1 | 12 | 140° C., 1 hour | 30 | 5.34 |
| Example 4 | Example 1 | 4.1 | 12 | 180° C., 30 minutes | 30 | 5.36 |
| Example 5 | Example 1 | 4.1 | 12 | 220° C., 30 minutes | 30 | 5.38 |
| Example 6 | Example 2 | 4.1 | 12 | 220° C., 30 minutes | 30 | 5.39 |
| Example 7 | Example 1 | 4.1 | 12 | 200° C., 10 minutes | 30 | 5.40 |
| Comparative Example 6 | Comparative Example 1 | — | 12 | 180° C., 30 minutes | 30 | 5.62 |
| Comparative Example 7 | Comparative Example 2 | — | 12 | 180° C., 30 minutes | 5 | 5.45 |
| Comparative Example 8 | Comparative Example 3 | 4.1 | 12 | 140° C., 1 hour | 30 | 5.22 |
| Comparative Example 9 | Comparative Example 3 | 4.1 | 12 | 180° C., 30 minutes | 30 | 5.37 |
| Comparative Example 10 | Comparative Example 3 | 4.1 | 12 | 220° C., 30 minutes | 30 | 5.38 |
| Comparative Example 11 | Comparative Example 4 | 4.1 | 12 | 220° C., 30 minutes | — | 5.39 |
| Comparative Example 12 | Comparative Example 5 | 4.1 | 12 | 220° C., 30 minutes | — | 5.28 |

As shown in Table 1, the thin film (Comparative Example 6) formed by use of the varnish obtained in Comparative Example 1 is greater in Ip value than the thin films of the other Comparative Examples, from which it is presumed that the ratio between ox-PTA and 5-SSA is changed owing to the precipitation of the solid matters during the operation of preparing the varnish and the removal of the solid matters by filtration.

The thin film (Comparative Example 7) formed by use of the varnish obtained in Comparative Example 2 is very thin, from which it is presumed that there is the high possibility that most solid matters are removed by filtration upon preparation of the varnish.

It is considered that the thin film (Comparative Example 8) obtained by baking at 140° C. for 1 hour by use of the varnish (using a reduced PTA) obtained in Comparative Example 3 is so low in Ip as not to permit the oxidation reaction to proceed satisfactorily when compared with the case where ox-PTA is used and baked at 220° C. for 30 minutes. On the other hand, it will be seen that the charge-transporting thin film (Example 3) obtained by baking at 140° C. by use of ox-PTrA has not significant difference in Ip from the case where baking is effected at 220° C. for 30 minutes and exhibits high Ip at the lower baking temperature.

The Ip value of the thin film obtained in Example 7 is at 5.40 eV, from which it will be appreciated that this value is well high even though baking is not effected in air.

Example 8

Charge-Transporting Varnish

To a mixture of 50 mg (0.143 mmol) of ox-PTrA and 102 mg (0.107 mmol) of BDSO-3 prepared according to the method described in WO 2005/000832 Pamphlet and represented by the afore-indicated formula, 3.38 ml of DMI was added and stirred at room temperature for dissolution. Moreover, 0.85 ml of 1,2-propanediol, 2.79 ml of cyclohexanol melted by heating up to 50° C. and 1.69 ml of DMI were added to the mixture and stirred to obtain a greenish black transparent solution. The thus obtained solution was filtered through a PTFE filter having a pore size of 0.2 µm, whereupon filtration could be made without clogging, thereby obtaining a greenish black transparent charge-transporting varnish.

Example 9

Charge-Transporting Varnish

To a mixture of 20 mg (0.057 mmol) of ox-PTrA obtained in Synthetic Example 1, 20 mg (0.057 mmol) of PTrA obtained in the first step of Synthetic Example 1 and 81 mg (0.085 mmol) of BDSO-3, 2.69 ml of DMI was added and stirred at room temperature for dissolution. Moreover, 0.68 ml of propylene glycol and 2.22 ml of cyclohexanol melted by heating up to 50° C. were added to the mixture and stirred to obtain a greenish black transparent solution. The thus obtained solution was filtered through a PTFE filter having a pore size of 0.2 μm, whereupon filtration could be made without clogging, thereby obtaining a greenish black transparent charge-transporting varnish.

Example 10

Charge-Transporting Varnish

To a mixture of 51 mg (0.146 mmol) of ox-PTrA obtained in Synthetic Example 1 and 98 mg (0.109 mmol) of NSO-2 prepared according to the method described in WO 2006/025342 Pamphlet and represented by the afore-indicated formula, 1.95 ml of DMI was added and stirred at room temperature for dissolution. Moreover, 3.27 ml of cyclohexanol melted by heating up to 50° C. was added to the mixture and stirred to obtain a greenish black transparent solution. The thus obtained solution was filtered through a PTFE filter having a pore size of 0.2 μm, whereupon filtration could be made without clogging, thereby obtaining a greenish black transparent charge-transporting varnish.

Comparative Example 13

Charge-Transporting Varnish

To a mixture of 50 mg (0.113 mmol) of PTA (reduced) and 107 mg (0.113 mmol) of BDSO-3, 1.74 ml of DMI was added and stirred at room temperature for dissolution. Moreover, 0.94 ml of 1,2-propanediol and 2.87 ml of cyclohexanol melted by heating up to 50° C. were added to the mixture and stirred to obtain a light green transparent solution. The thus obtained solution was filtered through a PTFE filter having a pore size of 0.2 μm, whereupon filtration could be made without clogging, thereby obtaining a charge-transporting varnish of a light green transparent solution.

Example 11

Charge-Transporting Thin Films

The varnish obtained in Example 8 was used to form charge-transporting thin films according to the respective methods described in Examples 3 to 5. The thus obtained charge-transporting thin films were made of a uniform amorphous solid.

Example 12

Charge-Transporting Thin Films

The varnish obtained in Example 9 was used to form charge-transporting thin films according to the respective methods of Examples 3 to 5. The thus obtained charge-transporting thin films were made of a uniform amorphous solid.

Example 13

Charge-Transporting Thin Films

The varnish obtained in Example 10 was used to form charge-transporting thin films according to the respective methods of Examples 3 to 5. The thus obtained charge-transporting thin films were made of a uniform amorphous solid.

Comparative Example 14

Charge-Transporting Thin Film

The varnish obtained in Comparative Example 13 was used to form charge-transporting thin films according to the respective methods of Comparative Examples 8 to 10. The thus obtained charge-transporting thin films were made of a uniform amorphous solid.

Examples 14 to 17

OLED Devices

The varnish obtained in Example 8 was spin coated onto an ITO glass substrate treated under the same conditions as in Example 3 and baked in air under different conditions indicated in Table 2 to form hole-transporting thin films. The substrate formed thereon with the thin film was introduced into a vacuum deposition apparatus, followed by successive deposition of α-NPD, Alq$_3$, LiF and Al, to provide an OLED device. The film thicknesses were, respectively, at 35 nm, 50 nm, 0.5 nm and 100 nm and the deposition operations were carried out after the pressure arrived at $8 \times 10^{-4}$ Pa or below. The deposition rate at 0.35 to 0.40 nm/second for α-NPD and Alq$_3$ and at 0.015 to 0.025 nm/second for LiF and at 0.2 to 0.4 nm/second for Al. Movement between deposition operations was made in vacuum.

Example 18

The varnish obtained in Example 9 was spin coated onto an ITO glass substrate treated under the same conditions as in Example 3 and baked in air under conditions indicated in Table 2 to form a hole-transporting thin film. This thin film was used to make an OLED device in the same manner as in Example 14.

Example 19

The varnish obtained in Example 10 was spin coated onto an ITO glass substrate treated under the same conditions as in Example 3 and baked in air under conditions indicated in Table 2 to form a hole-transporting thin film. This thin film was used to make an OLED device in the same manner as in Example 14.

Example 20

The varnish obtained in Example 10 was spin coated onto an ITO glass substrate treated under the same conditions as in Example 3 and baked in air under conditions indicated in Table 2 to form a hole-transporting thin film. The resulting thin film was introduced into a nitrogen glove box (an oxygen concentration of 10 ppm or below), and a 1.5 wt % xylene solution of a polymeric blue light-emitting material (SPB-02T, made by Merck & Co., Ltd.) was dropped over the thin film, spin coated and baked to form a 70 nm thick emission layer. The resulting laminated film attached ITO substrate was introduced into a vacuum deposition apparatus whose pressure was reduced to $5 \times 10^{-4}$ Pa or below, followed by successive vacuum deposition of barium (thickness: 0.9 nm) as a cathode and silver (thickness: 130 nm) to make a PLED device.

Comparative Examples 15, 16

OLED Devices

The varnish obtained in Comparative Example 9 was spin coated onto an ITO glass substrate treated under the same conditions as in Example 3 and baked in air under different conditions indicated in Table 2 to form a hole-transporting thin film. Subsequently, the substrate on which the thin film had been formed was introduced into a vacuum deposition apparatus, followed by successive vacuum deposition of α-NPD, $Alq_3$, LiF and Al under the same conditions as in Example 14 to provide OLED devices.

Comparative Example 17

OLED Device

An ITO glass substrate treated under the same conditions as in Example 3 was introduced into a vacuum deposition apparatus, followed by successive vacuum deposition of α-NPD, $Alq_3$, LiF and Al under the same conditions as in Example 14 to provide an OLED device.

Comparative Example 18

OLED Device

An ITO glass substrate treated under the same conditions as in Example 3 was introduced into a vacuum deposition apparatus, and copper-phthalocyanine (CuPC) was vacuum deposited thereon in a thickness of 25 nm, followed by successive vacuum deposition of α-NPD, $Alq_3$, LiF and Al under the same conditions as in Example 14 to provide an OLED device. The degree of vacuum and deposition rate for deposition of CuPC were same as those for A-NPD and $Alq_3$.

Comparative Example 19

OLED Device

A polyethylene dioxythiophene-polystyrenesulfonic acid aqueous solution (PEDOT, CH8000 made by Bayer AG) was spin coated onto an ITO glass substrate treated under the same conditions as in Example 3 and baked in air under conditions indicated in Table 2 to form a uniform hole-transporting thin film.

Moreover, α-NPD, $Alq_3$, LiF and Al were successively vacuum deposited under the same conditions as in Example 14 to make an OLED device.

The characteristics of the organic EL devices obtained in Examples 14 to 20 and Comparative Examples 15 to 19 are also shown in Table 2.

It will be noted that the device characteristics were measured by use of an organic EL emission efficiency measuring device (EL 1003, made by Precise Gauges Co., Ltd.).

TABLE 2

|  | Kind of varnish | Film thickness (nm) | Baking conditions | Current density (mA/cm$^2$) | Voltage (V) | Luminance (cd/m$^2$) | Current efficiency (cd/A) |
| --- | --- | --- | --- | --- | --- | --- | --- |
| Example 14 | Example 8 | 30 | 140° C., 1 hour | 175 | 7.0 | 5836 | 3.3 |
| Example 15 | Example 8 | 30 | 160° C., 1 hour | 259 | 7.0 | 9280 | 3.6 |
| Example 16 | Example 8 | 30 | 180° C., 1 hour | 236 | 7.0 | 7920 | 3.4 |
| Example 17 | Example 8 | 30 | 220° C., 30 minutes | 216 | 7.0 | 7542 | 3.5 |
| Example 18 | Example 9 | 30 | 180° C., 1 hour | 187 | 7.0 | 7179 | 3.8 |
| Example 19 | Example 10 | 30 | 220° C., 15 minutes | 54.6 | 7.0 | 1605 | 3.4 |
| Example 20 | Example 10 | 50 | 220° C., 15 minutes | 188 | 7.0 | 3043 | 1.6 |
| Comparative Example 15 | Comparative Example 13 | 30 | 140° C., 1 hour | 0.14 | 7.0 | 5.3 | 3.8 |
| Comparative Example 16 | Comparative Example 13 | 30 | 220° C., 30 minutes | 256 | 7.0 | 9760 | 3.8 |
| Comparative Example 17 | — | — | — | 0.37 | 7.0 | 1.2 | 0.32 |
| Comparative Example 18 | CuPC | 25 | — | 53.1 | 7.0 | 1572 | 3.0 |
| Comparative Example 19 | PEDOT | 40 | 120° C., 1 hour | 11.4 | 7.0 | 253 | 2.2 |

As shown in Table 2, it will be seen that the characteristics of the OLED device obtained in Example 14 are higher in current value at a voltage of 7.0 V than the OLED device obtained in Comparative Example 15, with the hole injection characteristic at the time of baking at 140° C. being higher. More particularly, it will be seen that with a charge-transporting thin film whose Ip is so low as not to permit the oxidation reaction to proceed satisfactorily, the hole injection characteristic is low.

The OLED devices obtained in Comparative Examples 17 to 19 are inferior to the devices obtained in Examples 14 to 19 with respect to the characteristics including a current density, luminance and current efficiency at a voltage of 7.0 V.

It will be seen that the PLED device obtained in Example 20 exhibits a high luminance at a low voltage like the OLED devices.

Example 21

Vacuum Deposition ox-PTrA obtained in Example 1 was introduced into a crucible on a vacuum deposition source of a vacuum deposition apparatus, made by Aoyama Engineering Corporation, followed by reduction in pressure to $5\times10^{-4}$ Pa or below. An electric current of 10 to 12 A was passed to filaments of the vacuum evaporation source (FB-2, made by Japan Vacs Metal Co., Ltd.) to heat the crucible, whereupon vacuum deposition started to form a 50 nm thick thin film on a quartz substrate.

UV-VIS (wavelength: 250 to 800 nm) absorption peak wavelength: 310 nm, 583 nm

The invention claimed is:

1. A charge-transporting varnish comprising the charge-transporting material consisting of a phenylamino-N,N'-diphenylquinonediimine derivative represented by the formula (1)

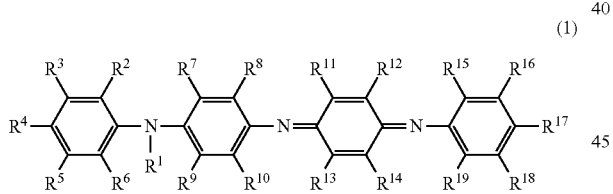

(1)

wherein $R^1$ represents a hydrogen atom, a methyl group or an ethyl group, $R^2$ to $R^{19}$ independently represent a hydrogen atom, a hydroxyl group, a silanol group, a thiol group, a carboxyl group, a phosphoric acid group, a phosphate ester group, an ester group, a thioester group, an amide group, a nitro group, a substituted or unsubstituted monovalent hydrocarbon group, an organooxy group, an organosilyl group, an organothio group, an acyl group, a sulfone group or a halogen atom.

2. The charge-transporting varnish according to claim 1, wherein $R^1$ to $R^{19}$ are each a hydrogen atom.

3. The charge-transporting varnish according to claim 2, wherein said varnish comprises a 1,4-benzodioxanesulfonic acid compound represented by the formula (8), a 1,4-benzodioxanesulfonic acid compound represented by the formula (9), a 1,4-benzodioxane compound having repeating units represented by the formula (10), or a 1,4-benzodioxane-sulfonic acid compound having repeating units represented by the formula (11):

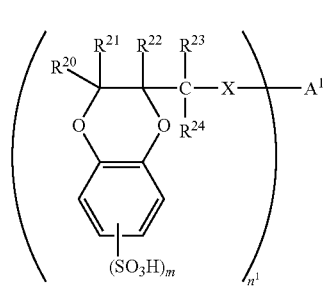

(8)

wherein $R^{20}$ to $R^{24}$ independently represent a hydrogen atom, a substituted or unsubstituted monovalent hydrocarbon group or a halogen atom, X represents a single bond, O, S or NH, $A^1$ represents a hydrogen atom, a halogen atom provided that X is a single bond, S provided that X is a single bond, an S(O) group, an S($O_2$) group, an N, Si, P or P(O) group unsubstituted or bonded with a substituent group, a substituted or unsubstituted hydrocarbon group, a 1,3,5-triazine group or a substituted or unsubstituted group represented by the following formula (12) or (13)

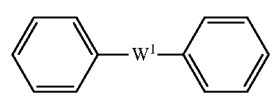

(12)

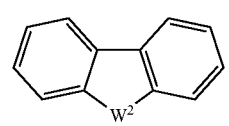

(13)

wherein $W^1$ and $W^2$ independently represent an O, S, S(O) group, an S($O_2$) group, or an N, Si, P or P(O) group unsubstituted or bonded with a substituent group, $n^1$ is an integer that is equal to the valence of $A^1$ and satisfies the relation of $1 \le n^1$, and m is the number of sulfonic acid groups bonded to a benzene ring moiety of the 1,4-benzodioxane skeleton,

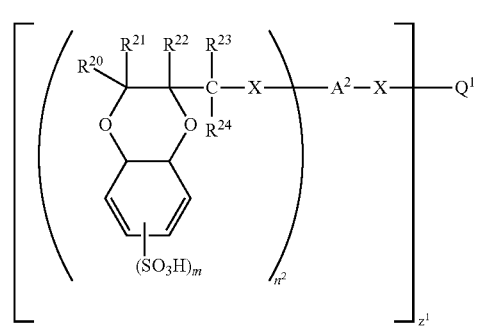

(9)

wherein $R^{20}$ to $R^{24}$, X and m, respectively, have the same meanings as defined above, $A^2$ represents a substituted or unsubstituted divalent or higher valent hydrocarbon group, a divalent or trivalent 1,3,5-triazine group or a substituted or unsubstituted group represented by the above-indicated formula (12) or (13), $Q^1$ represents a hydrogen atom, a halogen atom provided that X is a single bond, S provided that X is a single bond, an S(O) group, an S(O$_2$) group, an N, Si, P or P(O) group unsubstituted or bonded with a substituent group, a substituted or unsubstituted hydrocarbon group, a 1,3,5-triazine group or a substituted or unsubstituted group represented by the above-indicated formula (12) or (13), $n^2$ is an integer that is equal to (the valence of $A^2-1$) and satisfies the relation of $1 \le n^2$, and $z^1$ is an integer that is equal to the valence of $Q^1$ and satisfies the relation of $1 \le z^1$,

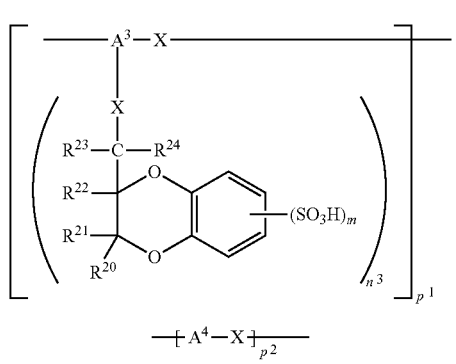
(10)

wherein $R^{20}$ to $R^{24}$, X and m, respectively, have the same meanings as defined above, $A^3$ represents a substituted or unsubstituted, trivalent or higher valent hydrocarbon group, a trivalent 1,3,5-triazine group or a substituted or unsubstituted group represented by the above-indicated formula (12) or (13), $A^4$ represents a substituted or unsubstituted, divalent or higher valent hydrocarbon group, a divalent or trivalent 1,3,5-triazine group or a substituted or unsubstituted group represented by the above-indicated formula (12) or (13), $n^3$ is an integer that is equal to (the valence of $A^3-2$) and satisfies the relation of $1 \le n^3$, $p^1$ is an integer satisfying the relation of $1 \le p^1$, and $p^2$ is an integer satisfying the relation of $0 \le p^2$ provided that $1 \le p^1 + p^2 \le 10000$ is satisfied, or

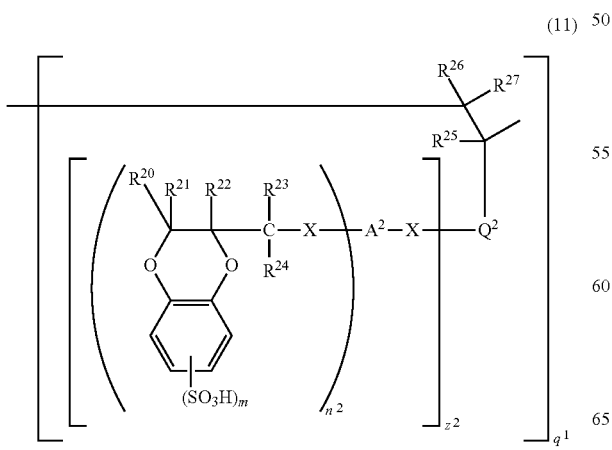
(11)

-continued

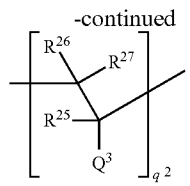

wherein $R^{20}$ to $R^{24}$, $A^2$, X, m and $n^2$, respectively, have the same meanings as defined above, $R^{25}$ to $R^{27}$ independently represent a hydrogen atom, a substituted or unsubstituted monovalent hydrocarbon group or a halogen atom, $Q^2$ represents a substituted or unsubstituted, divalent or higher valent hydrocarbon group, a divalent or trivalent 1,3,5-triazine group or a substituted or unsubstituted group represented by the afore-indicated formula (12) or (13), $Q^3$ represents a substituted or unsubstituted hydrocarbon group, a 1,3,5-triazine group or a substituted or unsubstituted group represented by the afore-indicated formula (12) or (13), $z^2$ is an integer that is equal to (the valence of $Q^2-1$) and satisfies the relation of $1 \le z^2$, $q^1$ is an integer satisfying the relation of $1 \le q^1$ and $q^2$ is an integer satisfying the relation of $0 \le q^2$ provided that $1 \le q^1 + q^2 \le 10000$.

4. The charge-transporting varnish according to claim 2, comprising an arylsulfonic acid compound represented by the formula (14) or (15)

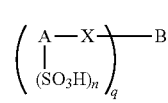
(14)

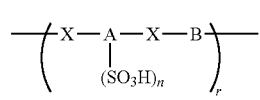
(15)

wherein X represents O, S or NH, A represents X, or a naphthalene ring or an anthracene ring which may have a substituent other than an n number of (SO$_3$H) groups, B represents a substituted or unsubstituted hydrocarbon group, a 1,3,5-triazine group, or a substituted or unsubstituted group represented by the following formula (12) or (13)

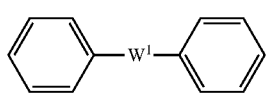
(12)

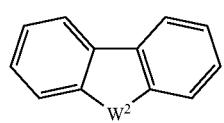
(13)

wherein $W^1$ and $W^2$ independently represent O, S, an S(O) group, an S(O$_2$) group or an N, Si, P or P(O) group unsubstituted or bonded with a substituent group, n is the number of sulfonic acid groups bonded to A and is an integer satisfying $1 \le n \le 4$, q indicates the number of bonds between B and X and is an integer satisfying $1 \le q$, and r indicates the number of repeating units and is an integer of satisfying $1 \le r$.

5. A charge-transporting thin film made by use of the charge-transporting varnish defined in claim 2.

6. A charge-transporting thin film comprising the charge-transporting material defined in claim 1.

7. An organic electroluminescent device comprising the charge-transporting thin film defined in claim 5 or 6.

8. A method for preparing the phenylamino-N,N'-diphenylquinonediimine represented by the formula (1) in claim 1, said method comprising reacting a 4-hydroxydiphenylamine compound represented by the formula (2) or (3)

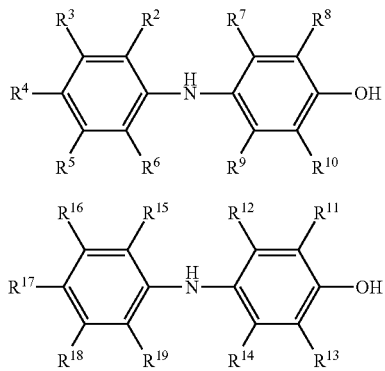

(2)

(3)

wherein $R^2$ to $R^{19}$, respectively, have the same meanings as defined in claim 1, with a 4-aminodiphenylamine represented by the formula (4) or (5)

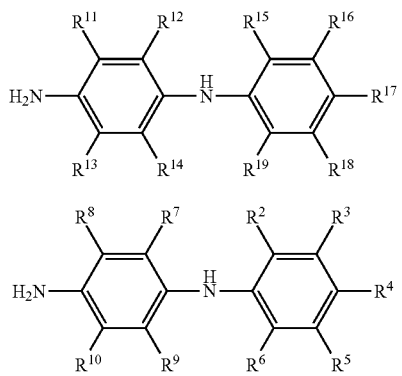

(4)

(5)

wherein $R^2$ to $R^{19}$, respectively, have the same meanings as defined in claim 1 in the presence of a titanium alkoxide catalyst to prepare a phenyltetraaniline compound represented by the formula (6)

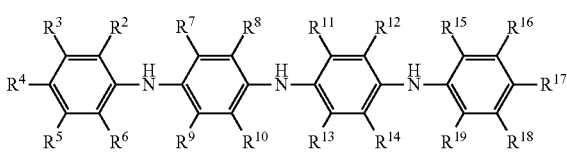

(6)

wherein $R^2$ to $R^{19}$, respectively, have the same meanings as defined in claim 1, and further treating with an oxidizing agent to give the phenylamino-N,N'-diphenylquinonediimine represented by the formula (1).

9. The charge-transporting varnish according to claim 1, wherein said varnish comprises (A) one or more organic solvents selected from the group consisting of methanol, N,N-dimethylformamide, N,N-dimethylacetamide, N-methylpyrrolidone, dimethylsulfoxide, chloroform and toluene, and (B) one or more organic solvents selected from the group consisting of cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, 1,2-propanediol, 1,3-propanediol, hexylene glycol, butyl cellosolve, diethylene glycol diethyl ether, dipropylene glycol monomethyl ether, ethyl carbitol, methyl carbitol, diacetone alcohol, γ-butyrolactone, ethyl lactate, acetonitrile, ethanol, n-propanol, t-butanol, 2-butanone, carbon disulfide and nitromethane.

* * * * *